US012193699B2

(12) United States Patent
Wiita et al.

(10) Patent No.: US 12,193,699 B2
(45) Date of Patent: *Jan. 14, 2025

(54) ADJUSTABLE RING STRIPPER FOR MORE EFFICIENTLY AND EFFECTIVELY REMOVING PLAQUE FROM ARTERIES

(71) Applicant: ENDOVASCULAR INSTRUMENTS, INC., Casper, WY (US)

(72) Inventors: Thomas A. Wiita, Jackson, WY (US); Thomas L. Kelly, Camas, WA (US)

(73) Assignee: ENDOVASCULAR INSTRUMENTS, INC., Casper, WY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/069,369

(22) Filed: Dec. 21, 2022

(65) Prior Publication Data
US 2023/0119672 A1    Apr. 20, 2023

Related U.S. Application Data

(63) Continuation of application No. 17/845,162, filed on Jun. 21, 2022, now Pat. No. 11,534,198, which is a continuation of application No. 15/330,355, filed on Sep. 9, 2016, now Pat. No. 11,839,398.

(51) Int. Cl.
| | |
|---|---|
| A61B 17/3207 | (2006.01) |
| A61B 17/3205 | (2006.01) |
| A61B 17/32 | (2006.01) |
| A61F 2/07 | (2013.01) |
| A61F 2/958 | (2013.01) |

(52) U.S. Cl.
CPC ......... *A61B 17/320725* (2013.01); *A61B 17/32056* (2013.01); *A61B 17/3207* (2013.01); *A61B 2017/320008* (2013.01); *A61B 17/320708* (2013.01); *A61B 2017/320741* (2013.01); *A61B 17/32075* (2013.01); *A61F 2/07* (2013.01); *A61F 2002/072* (2013.01); *A61F 2/958* (2013.01)

(58) Field of Classification Search
CPC ...... A61B 17/320725; A61B 17/32056; A61B 17/3207; A61B 17/320708; A61B 17/32075; A61B 2017/320008; A61B 2017/320741; A61F 2/07; A61F 2/958; A61F 2002/072
See application file for complete search history.

(56) References Cited

U.S. PATENT DOCUMENTS

| | | |
|---|---|---|
| 2,944,552 A | 7/1960 | Cannon |
| 3,730,185 A | 5/1973 | Cook et al. |
| 3,811,446 A | 5/1974 | Lerwick et al. |
| 4,315,511 A | 2/1982 | Chin |
| 5,084,054 A | 1/1992 | Bencini et al. |
| 5,480,379 A | 1/1996 | La |
| 5,571,169 A | 11/1996 | Plaia et al. |
| 5,820,629 A | 10/1998 | Cox |
| 5,843,102 A | 12/1998 | Kalmann et al. |
| 6,146,397 A | 11/2000 | Harkrider |
| 6,241,745 B1 | 6/2001 | Rosenthal |
| 8,579,927 B2 | 11/2013 | Witts et al. |
| 2001/0041899 A1 | 11/2001 | Foster |

(Continued)

*Primary Examiner* — Jing Rui Ou
(74) *Attorney, Agent, or Firm* — DORSEY & WHITNEY LLP

(57) ABSTRACT

An adjustable loop stripper for stretching an arterial wall outwardly as plaque is excavated inwardly.

18 Claims, 19 Drawing Sheets

(56) References Cited

U.S. PATENT DOCUMENTS

| | | |
|---|---|---|
| 2002/0029052 A1 | 3/2002 | Evans et al. |
| 2002/0120257 A1 | 8/2002 | Newman et al. |
| 2003/0018355 A1 | 1/2003 | Goto et al. |
| 2004/0220604 A1 | 11/2004 | Fogarty et al. |
| 2011/0197732 A1 | 8/2011 | Tatat et al. |
| 2013/0006262 A1* | 1/2013 | Lampropoulos ....... A61B 17/50 606/113 |
| 2014/0296889 A1 | 10/2014 | Avneri et al. |
| 2017/0007279 A1 | 1/2017 | Sharma |

* cited by examiner

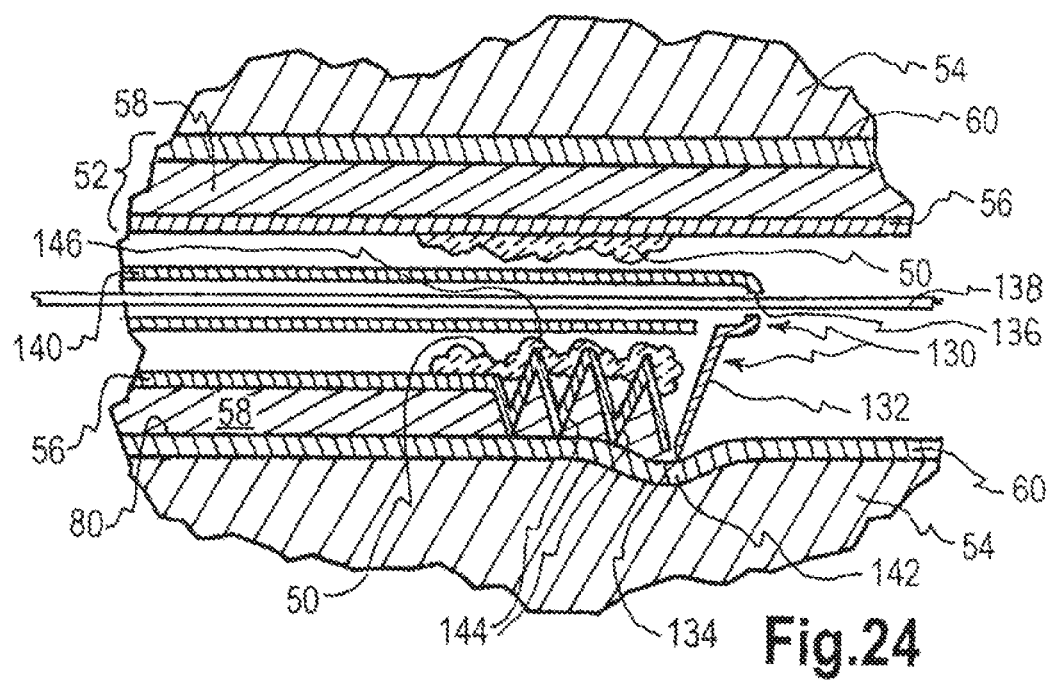
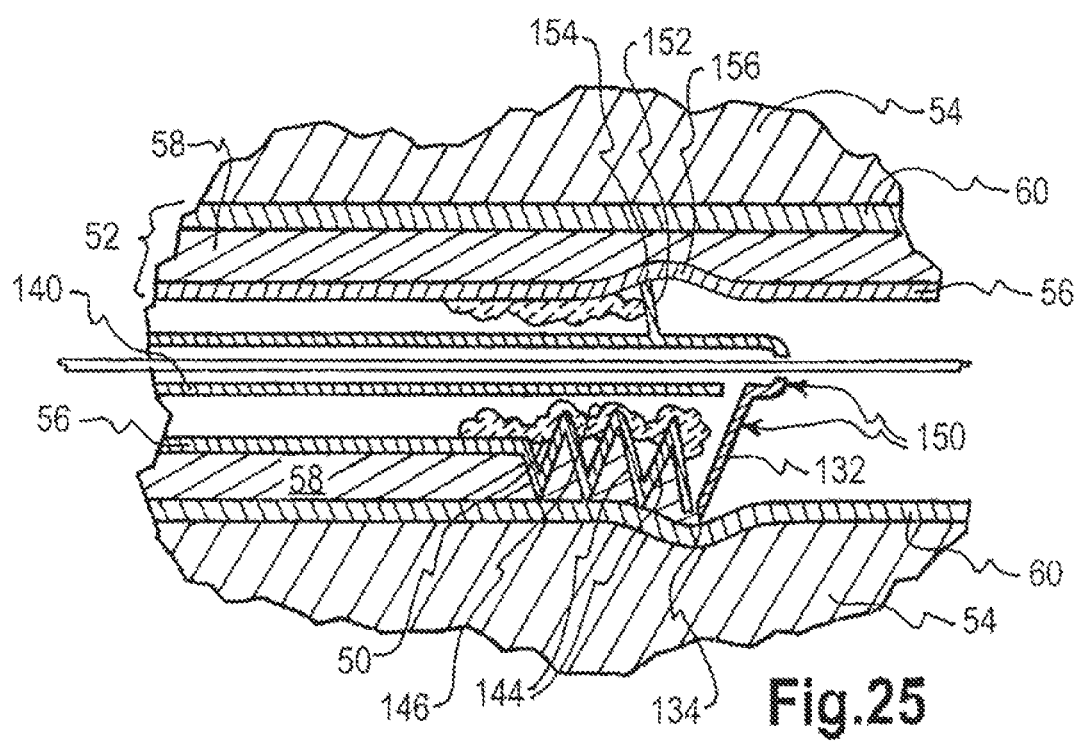

ADJUSTABLE RING STRIPPER FOR MORE EFFICIENTLY AND EFFECTIVELY REMOVING PLAQUE FROM ARTERIES

RELATED APPLICATIONS

This application is a continuation of U.S. patent application Ser. No. 17/845,162, filed on 21 Jun. 2022, now U.S. Pat. No. 11,534,198, which is a continuation of U.S. patent application Ser. No. 15/330,355, filed on 9 Sep. 2016, now U.S. Pat. No. 11,839,398, the disclosures of which are incorporated, in their entireties, by this reference.

FIELD OF THE INVENTION

The present invention relates generally to the treatment of atherosclerotic plaque on the walls of arteries and, more particularly, to an adjustable ring stripper, and related methodology, by which deposits of plaque are more efficiently and more effectively removed from arteries.

BACKGROUND

Heart disease, notwithstanding the advances of modern medicine, is the underlying cause of coronary artery disease, which accounts for about 50% of all deaths in the United States annually. Plaque build-up in arteries underwrites this high mortality rate. The mortality rate would be noticeably high but for present day treatments to remove plaque, or to by-pass blockage or otherwise cause the blood flow path in a diseased artery to be enlarged. The medical profession, perhaps on a risk-benefit basis, has endorsed and adopted a singular practice of choosing one only of the several strategies for treating heart disease, e.g. by-pass or balloon dilation or plaque removal. Yet the treatment results are, overall, mixed, with restenosis being an on-going concern. So, the medical search has continued, with the goal of finding more effective and more efficient instruments and procedures for treating heart disease, including atherosclerotic plaque. Atherosclerotic plaque on the wall of the artery, which restricts and reduces or eliminates blood flow, eventually produces problems for the patient. These underlying disease mechanisms are of major importance to the healthcare system. This disease attacks many, if not all, arteries, including the carotid arteries, which supply blood to the brain. This disease is involved as a cause of strokes, another leading cause of death. It also develops in the femoral arteries, the blood supply for the legs, and causes Peripheral Arterial Disease (PAD), which can lead to circulatory problems, pain with exercise, rest pain, and even tissue loss and ultimately amputations. This disease process is progressive, in that these deposits continue to build up, the blood flow pathway continues to narrow and progressively become restricted, and produce changing and increasingly severe symptoms.

Many different treatments have been developed for this disease, including balloon angioplasty, where a balloon is inflated to dilate the narrowed plaque infested section an artery to enlarge the fluid pathway. Stents are sometimes placed in these diseased arteries, which are cylinders made of wire mesh that expand and push outward to hold open (dilate) a narrowed section of the artery and provide increased blood flow. Bypass surgery is sometimes performed to treat this disease, where a cylindrical conduit for blood flow made of various materials, including vein or synthetic graft materials, is placed surgically and connected to the artery at two points, with the blood flow rerouted from the artery into and back out of the conduit into the artery. This routes the blood flow around the blockage. Stents and grafts are sometimes used to treat particular kinds of lesions in particular arteries. It is not unusual for patients to have successive treatments, either because the prior treatment failed and is no longer allowing the blood to flow, or because disease progression has produced further narrowing in the vessel that now requires another treatment. Treating previously treated patients at a later point in time presents new, different and difficult problems and challenges in terms of the devices and methods used, compared to performing the first, "de novo" treatment.

One strategy for treating these blockages in arteries is to remove the atherosclerotic plaque deposits from the artery. Many methods and devices have been developed to remove this plaque. These devices and methods are designed for use in specific vessels, and/or at specific points in the progression of the disease, and/or after specific prior treatments have been performed, which, in turn, have failed. Some of these devices involve the use of a guidewire. Some of these plaque removal devices, e.g., MollRing cutter, do not involve the use of a guidewire, so that when the device may be inserted into the artery eccentrically doing damage to the artery, e.g. perforation of the artery wall and otherwise be less safe than an "over the guidewire" device, which follows the guidewire and thus stays more concentric in the vessel, causing less trauma to the vessel wall.

Each of these treatments are performed as one continuous treatment only. For example, dilating the blocked artery with an angioplasty balloon, when used, is intended to be the only, final and complete treatment for the blocked artery. Also, removing the plaque by dissection, when used, is intended to be the only, final and complete treatment for the blocked artery.

Approximately 75% of plaque is eccentric in the vessel, so that the arterial lumen through which the blood flows in an occluded vessel is located off-center in respect to the vessel wall. In the vessel dilation, whether accomplished using an angioplasty balloon or a set of dottering sheaths or a vessel dilator, typically the expansion process creates a spiral fracture that begins in the inner lumen of the plaque, spirals outward and terminates at the vessel wall. As the expansion/dilation process proceeds, a portion of the plaque, typically at the outer end of this fracture, where the plaque tapers to a very thin dimension, becomes loosened from the vessel wall. As the expansion reaches its maximum, a portion of the plaque slides along the vessel wall circumferentially, causing the plaque to become loosened from the wall. Typically this loosening occurs around a portion, but not all, of the circumference of the vessel, as the thicker plaque, because of the eccentricity, remains anchored to the vessel wall. This is a variable, and sometimes the loosening can be nearly complete, sometimes only partial. Overall, the plaque and the vessel wall are typically weakly attached. Vascular surgeons take advantage of this weak attachment when they perform blunt dissection to separate the arterial wall from the plaque during carotid endarterectomy, for example, and similar procedures. Surgeons know firsthand, as they have held plaque and vessel walls in their gloved fingers. Sometimes the plaque and the vessel wall become integrated with each other, and the attachment between the two can become very strong.

Vessel dilatation can be accomplished with angioplasty balloons or vessel dilators. Dilators use the principle of dottering, in which a tapered, cone-shaped hard object is inserted into a narrowed portion of a vessel. As the tapered nose of the object is advanced through the narrowed portion of the vessel, the taper forces the plaque material to expand at least to the minimum size that permits the tapered device to pass through the narrowed area. In Charles Dotter's original conception, after a first dilator with a tapered tip was advanced, a second tight fitting sheath with a tapered tip was advanced over the first, which produced a second enlarging step of dilation.

Balloon catheters produce a similar result, but the force they exert is limited to the maximum pressure rating of the balloon. Since some plaque is fibrous and/or calcified and quite strong, sometimes a balloon cannot crack open and dilate such plaque. The angiographic sign that this is the case is called "wasp wasting", where the balloon fills fully but not in one area so that the balloon looks narrowed and not fully expanded in that highly resistant plaque area. The not-fully-expanded balloon looks like an insect, namely a wasp, narrower in one section of the body than adjacent sections. That means that a dilation performed with a balloon would, in some cases, not completely dilate and loosen the plaque from the vessel wall.

The plaque removing devices mentioned above would not be helped to function better by pre-loosening of the plaque and such pre-loosening might even interfere with proper operation of a plaque removal device. The previously mentioned devices remove plaque starting in the lumen of the vessel and remove limited amounts of plaque sequential, by cutting off small amounts at a time or grinding off limited amounts of the plaque. If the plaque were pre-loosened, then the plaque removing device could break loose a piece of plaque that it could not capture and make it easier for such pieces of plaque to embolize and cause further problems and blockages, as blood flow carries such emboli downstream to smaller arteries.

There are plaque removal devices that are helpful to achieve easier and more complete plaque removal via-pre-loosening of the plaque. One such device is an Endarterectomy Catheter. Another is a finger nail plaque remover by Dr. LeRoy Groshong. Both of these devices pull the plaque out of the vessel. Such removal is helped if the plaque is not firmly adherent to the vessel wall, but already loosened from the wall. Both devices are made in "over the guidewire" configurations and, as such, have the benefits of greater safety and less damage to the arterial wall as compared to not-over-the-guidewire devices. Over-the-wire devices have a lumen through which the guidewire is passed causing the device to follow the guidewire into the vessel in which the guidewire has been placed earlier.

An arterial blood vessel wall consists of three layers: (1) the innermost layer is the intima, a microscopically thin layer between the blood and the artery; (2) the media contiguous with the intima, which consists of muscular tissue comprised of smooth muscle cells which are elastic and stretchy and contain the arterial blood pressure and respond to expansion and contraction as required; and (3) the adventitia contiguous with the media, which is stretchy net-like tissue highly stretchable structure borders on the surrounding leg tissue and provides blood supply to the artery wall including the media. Plaque manifest itself between the intima and media, often invading and becoming one with the media.

Another approach to removing plaque from vessels is to use a ring stripper. Ring strippers were developed originally by DeBakey and Wylie, later improved by Cannon (the Cannon Ring Dissector) and then further improved by Vollmar (the Vollmar Ring). The earliest DeBakey device consisted of a ring mounted on the end of a long shaft. The ring was circular, oriented at right angles (90 degrees), to the longitudinal axis of the artery, and mounted on a long, thin, stiff shaft. Cannon improved this by orienting the ring diagonally at 105 degrees, and Vollmar improved the device further by additionally elongating the ring and orienting this elongated ring diagonally at 135 degrees to the longitudinal axis of the vessel. Both of these later devices look circular when viewed looking down the longitudinal axis of the artery, but the elongated shape assists the user to probe and concentrate force distally in localized areas to aid in separating the plaque from the vessel wall.

All of these ring devices operate by dissection. Surgeons in general use two different kinds of dissection, sharp dissection and blunt dissection. In sharp dissection, a sharp instrument such as a scalpel cuts the tissue to dissect the tissue into two separate masses of tissue. In blunt dissection, a blunt instrument is advanced along a pre-existing cylindrical interface within the tissue, where it is easy to separate one mass of tissue from the other. An analogy would be to the grain in a piece of wood, where even a blunt ax or adz can split the wood into two separate masses because the wood naturally separates along an existing plane of weakness.

The ring is first carefully inserted into the cylindrical interface, where the plaque and the vessel wall meet, and then carefully advanced down the vessel, with the ring separating the vessel wall from the plaque along the interface. In general, the plaque is less elastic and the vessel wall is more elastic. As a result, what actually happens is that the vessel wall is being radially lifted off the plaque and stretched slightly as separation occurs.

The plaque, once separated from the wall, is cut and removed from the residual plaque further down the vessel. It is important to note that such patients have some layer of plaque throughout their arteries, even sections of artery that look angiographically normal, not just in the areas where the plaque deposit has grown thick and caused flow obstruction. Often the desired separation and removal happens just by using the ring, manipulating the ring by twisting or pulling to cause the plaque to separate and then the plaque can be removed. However, in many patients such manipulation does not cause the plaque to separate as desired, making for an unreliable treatment. The MollRing cutter was developed precisely to address this problem and provide a better way to cut this plaque from the residual plaque further down the vessel. The MollRing device was intended to perform both stripping and cutting, although some users would strip first using a ring such as the Vollmar, then cut using the Moll-Ring.

All such treatments leave behind a potentially dangerous situation where the residual plaque can be lifted off the vessel wall by the blood flow. This may cause a flap of plaque to fold or rotate across the flow path of the vessel and cause occlusion or closure of the vessel. After the development of stents, stents have been routinely employed to "tack up" and hold such potential flaps in place and prevent such occlusions or closures, which have the potential of a serious complication. And further still, the arterial wall does not respond well to stripping and becomes more prone to restenosis. With this protocol, the vessel wall has received an "insult" and responds by triggering spontaneous healing and prolific cell growth leading to early restenosis. Such excessive "early restenosis" has been reported in the relevant literature. In addition, such treatments do not have the safety and other benefits of being performed over a guidewire.

Thus, there remains a need for treatments for constricted or occluded arteries that: (1) have higher success rates; (2)

produce safer plaque removal; and (3) the treatment solves or help solve the problems of abrupt closure from residual plaque flaps and restenosis from irritated arterial wall as side effects of plaque removal. In this regard, the inadequacies of prior art ring strippers and improvements thereto are herein addressed.

BRIEF SUMMARY AND OBJECTS OF THE INVENTION

It is a primary object of the present invention to overcome or alleviate prior art problems of the past in the field of treatment of arterial plaque.

It is another paramount object to provide a novel adjustable ring stripper and related methodology from improved removal of plaque from a flow restricted artery.

These and other objects and features of the present invention will be apparent from the detailed description taken with reference to the accompanying drawings.

BRIEF DESCRIPTION OF THE DRAWINGS

FIG. 24 is a fragmentary longitudinal cross section of a plaque infested artery showing a reverse barb instrument for both debonding and excavating the plaque;

FIG. 25 is a fragmentary longitudinal cross section of a plaque infested artery showing a reverse barb instrument comprising two reverse barbs, by which plaque is debonded, excavated and removed from an artery;

DETAILED DESCRIPTION OF THE ILLUSTRATED EMBODIMENTS

Figure 1:
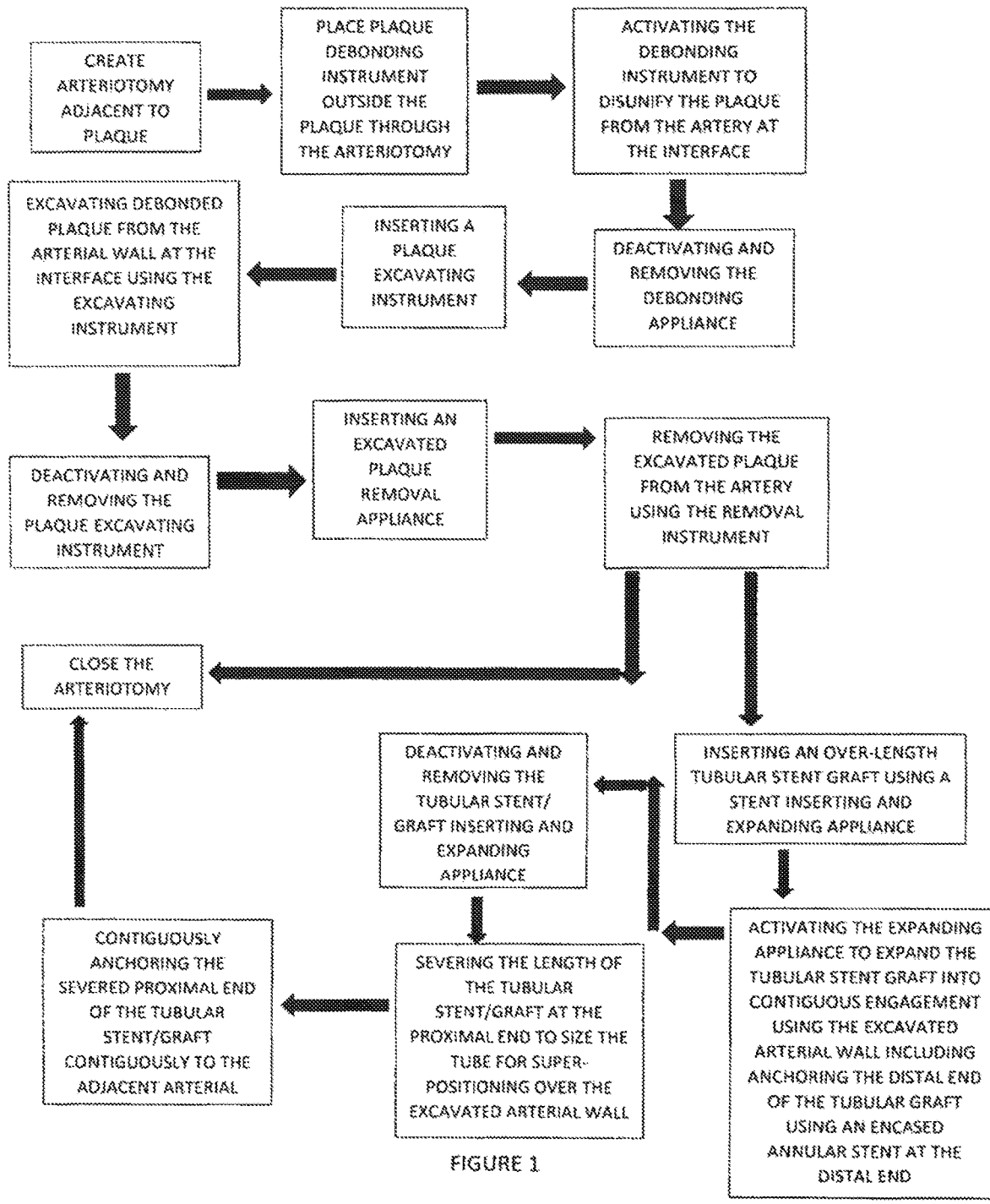
FIG. 1 is a block diagram, illustration certain aspects of the present invention.

The illustrated embodiments demonstrate and are representative of consecutive use of combinations of medical procedures, appliances and instruments and related methods by which a partially or totally occluded artery or other vessel of a patient is recanalized. While other advantages of the present invention exist, the present invention particularly addresses prior problems of post treatment inadequate blood flow, incomplete plaque removal and post treatment restenosis. Also, bridging of two graft portions, where actual length of the atherectomy exceeds to anticipated length of one graft has been problematic.

While the present invention may be used in a vessel other than an artery, the primary benefit lies in application to an artery. Arterial flow is either conduit or branch flow. The iliac, femoral, and more distal arteries are most likely to occlude, either totally or partially. All arteries are strong, durable, three-layer vessels while veins are thin, single layer conduits. The arterial wall layers are, inside out, the tunica intima endothelium (intima), the tunica media (media), and the tunica adventitia (adventitia). It has been found that in diseased arteries typically the interface between the adventitia layer and the media layer becomes a region of naturally occurring weakness. In fact, it has been found that plaque not only accumulates within the lumen of the artery but infiltrates both the intima and media causing a tissue breakdown there.

Removal of the plaque, intima and the media from the adventitia and leaving the adventitia as the flow path of the artery is called an endarterectomy.

The primary cause of arterial occlusion is build-up of atheroscelerotic plaque, the density of which ranges between very soft to rock-hard calcified deposits. Plaque deposits may form in some arteries and not at all or slightly in other arteries of the same person. A plaque deposit in a specific area or region of an artery is sometimes called an atheroma.

Under appropriate anesthesia the artery is exposed, occluded with a surgical clamp or vessel loop, and at least a single arteriotomy is performed distal to the clamp and proximal to the occlusion. Under some circumstances two arteriotomies are performed, one upstream and the other downstream of the atheroma although a single arteriotomy is preferred. In some situations, access to the artery can be by use of percutaneously placed hollow needle, instead of by use of an arteriotomy. The needle is then used to advance a guidewire, the needle removed, and a sheath/dilator is placed through the skin over the guidewire into the artery. The dilator is removed and the final result is a guidewire and sheath placed through the skin and into the artery, which can then be used to insert and remove a variety of devices including angioplasty balloons, stent delivery devices and stent/graft delivery devices.

In situations where an arteriotomy is the preferred choice, a guide wire is preferably advanced through an upstream arteriotomy until the guide wire extends beyond the atheroma. Sometimes a guide wire can be advanced through a clogged artery, but not always. In situations where a guide wire alone cannot cross the atheroma, a dynamic wire guide or a dynamic disrupter is preferably used to centrally loosen and/or displace the centrally disposed plaque, followed by central insertion of the guide wire through the hollow interior in the dynamic wire guide or disrupter. Thereafter, the dynamic wire guide or disrupter is removed.

Any technique by which the plaque is severed from the inner wall of the intima is called an atherectomy. Typically, plaque may be so severed by a coring catheter or by using an atherotome having one or more expandable blades to accommodate insertion and one or more passes through the atheroma, each pass at an increased blade diameter. Devices exist which remove plaque as intact cylinders.

Atherectomy devices such as a Simpson Atherocath, an Auth Rotablator, a Kensey device, or an Interventional Technologies Transluminal Extraction Catheter (TEC device) have been used in the past.

In some situations, an endarterectomy is the preferred medical choice. For example, an endarterectomy is often best when the disease of the artery is substantially advanced, causing a natural interface of weakness between the media and the adventitia. A cutting atherotome may be used to initially cut through the diseased intima and media to the adventitia at the distal end of the site of the endarterectomy creating a taper at that location followed by advancement in a proximal direction until the entire undesired length of plaque, intima and media have been excavated. Alternatively, the plaque, intima and media may be cut radially or on a bevel adjacent both a first and second arteriotomy located above and below the atheroma. Ideally, a taper is used at both ends of the endarterectomy where the enlarged lumen produced connects across a beveled taper to the normal lumen of the artery, both distally and proximally the dispensed material is loosened from the wall using any suitable instruments, such as a surgical spatula. Forceps may be used to grasp and pull upon a loosened part of the intima and media to be removed causing the intima and media between the two cuts together with the atheroma contained therein to be removed from the artery as a cylindrical or annular unit.

Alternatively, a Hall loop may be advanced from one arteriotomy to the other after the two above-mentioned cuts have been made. The loop, in the nature of a piano wire loop held on the end of a staff and activated by a motorized drive to produce a rotary oscillating motion of the wire loop is positioned at the above-mentioned natural interface of weakness. The loop is positioned at and displaced along the interface by pushing on the staff until the intima, the media, and the atheroma to be removed have been unitarily severed following which' the cylindrical or annular unit may be grasped and removed from the artery using forceps, for example.

Similarly, a Scanlan Endarsector or a cutter having rotating blades may be used to assist in the performance of the endarterectomy.

In situations where an angioplasty, in whole or in part, is the treatment of choice, an instrument of expansion is used to enlarge or open and enlarge the blood flow accommodating lumen at the atheroma. Mechanical instruments, equipment for performing balloon angioplasty, laser instruments, and instrumentation for ultrasound angioplasty may be used to achieve the angioplasty.

Once the plaque has been removed, steps may be taken to line the remaining treated arterial or vessel wall. The resulting lining is herein referred to as a vascular graft. Vascular graft, as used herein, is intended to mean any of the following: 1. conventional and novel artificial grafts made of any material, including but not limited to fabrics such as dacron, or expanded PTFE Goretex™ thin wall sleeve material, in any density from very soft and low density to very stiff and high-density, constructed in any shape including straight, tapered, or bifurcated, and which may or may not be reinforced with rings, spirals or other reinforcement, and which may or may not have one or more expandable stents incorporated into the graft at one or both ends or along its full length; 2. natural artery or vein material taken from human or animal donors; 3. stents; 4. covered stents in which the stent is covered with a variety of covering materials; 5. drug eluting stents in which a drug-containing coating is applied to the stent which releases the drug over time to prevent restenosis; 6. coating applied to the inside of the treated arterial wall which forms a patent lumen or is biologically active and causes the lining of the vessel or duct to form a patent lumen; and 7. any combination of the foregoing vascular graft options. The exterior of the vascular graft or part of it may and preferably does comprise tissue in-growth material. Where a pre-formed tubular vascular graft of synthetic material is used, the material thereof may be and preferably is dimensionally stable. However, if desired, it may be radially expandable material.

The vascular graft of choice may be introduced into the treated artery or other vessel in any suitable way including but not limited to use of a sheath/dilator, placement of the vascular graft upon a mandrel shaft and/or use of long-nose forceps, or by use of an angioplasty balloon catheter. The distal ends of the tubular graft and the mandrel shaft may be temporarily sutured together or the distal end of the vascular graft sutured together over the mandrel to accommodate unitary displacement into the vessel, for example through a sheath after the dilator has been removed.

Where the material of which the vascular graft is formed is expandable and in tubular or sleeve form, once the sheath has been removed the diametral size of the graft may be enlarged in contiguous relationship with the inside arterial surface using a balloon catheter. A balloon catheter may also be used to bring a folded or partially collapsed or expandable vascular graft which is dimensionally stable into contiguous relation with the interior surface of the remaining artery wall.

The tubular graft may also comprise a biologically inert or biologically active antistenotic coating applied directly to the treated area of the remaining arterial inner surface to define a lumen of acceptable blood flow capacity.

The graft, once correctly positioned and contiguous with the interior vascular wall, is usually believed to inherently secure it against inadvertent migration within the artery or other vessel due to friction and infiltration of weeping liquid accumulating on the inside artery wall. It is preferred that the length of the vascular graft be selected to span beyond all of the treated region of the artery and overlap into the untreated region so that none of the treated region is exposed to the blood flow since this can increase rates of restenosis, which is a resumption of the disease process that occluded the blood flow originally.

One or both ends of the vascular graft may be sutured or surgically stapled in position on the treated wall to prevent undesired displacement or partial or complete collapse under cardiovascular pressure. In particular, the upstream end of a graft placed in an artery must be secure to prevent a flap of the graft from being pushed, by arterial blood flow, into a position where it occludes, in whole or in part, the vessel. One or both ends may be held open by one or more stents disposed within the tubular graft. Forceps may be used to hold a free end of the vascular graft while the other end is secured to the vascular wall. Currently, it is preferred to secure the proximal end of the tubular vascular graft to the treated vascular wall and to bias dilate the distal end of the tubular vascular graft by use of a balloon catheter and/or arterial pressure. Where the distal exterior of the sleeve-shaped vascular graft comprises tissue ingrowth material, as is preferred as in-growth occurs it becomes immaterial how the initial dilating bias was achieved.

Persistent issues remain. Balloon angioplasty typically only expands the plaque short term, with restenosis continuing thereafter. Endarterectomies sometimes damage the residual arterial wall and/or often result in less than complete plaque removal. By-pass surgery is highly invasive and therefore, a high risk to the patient. Restenosis is a frequent problem leading to a second plaque treatment and further risks to the patient. Contrary to the past practices of those skilled in the art, including cardiovascular surgeons, one thesis for the present invention is the discovery that multiple medical techniques can be surprisingly effective, when utilized as a single surgical event to alleviate problems imposed in the past by confining treatment to a single medical technique.

Reference is now made to the drawings wherein like numerals are used to designate like parts throughout. In regard to FIG. 1, two aspects of the present invention are diagrammatically illustrated. Initially, for the purpose of treating plaque, the surgeon will make an arteriotomy proximal of one or more plaque deposits in the artery. Sometimes two arteriotomies are performed, one adjacent to each end of the plaque deposit.

Through the arteriotomy, the surgeon places a guidewire if needed later in the procedure the surgeon places a plaque debonding instrument into the artery and locates it either within the plaque deposit or in the interface between the plaque and the arterial wall. In instances where the plaque deposit occludes blood flow in the artery, known techniques exist for coring the plaque so that the debonding instrument and other instruments, as and to the extent needed, can be placed within a hollow existing in the plaque.

The debonding instrument, in some instances slideably mounted on a guidewire, is activated by the surgeon to disunify and destrengthen an existing bond between the plaque and the arterial wall at an interface. Some debonding instruments have a tapered leading section which dilates the plaque, thereby creating space inside the atheroma through which to advance the debonding instrument. Thereafter, the debonding instrument is deactivated and removed from the artery through the arteriotomy. Next, a plaque excavating instrument, preferably slideably mounted on a guidewire, is introduced into the artery through the arteriotomy whereby the debonded plaque is excavated along the interface between the arterial wall and the plaque.

Thereafter, the plaque excavating instrument is deactivated and removed and a plaque removal appliance, preferably slideably mounted on a guidewire, is appropriately introduced into the artery to displace the excavated plaque from the artery through the arteriotomy, at which time the plaque removal instrument is withdrawn through the arteriotomy. Thus, a plurality of medical protocols are used to reach this point in the plaque treatment process. While it is otherwise normally preferred, at this juncture, based upon the wisdom of the surgeon, the arteriotomy may be sutured closed and the treatment concluded.

Preferably, however, the arteriotomy is left open and an over length tubular graft with a distal stent incased therein is inserted through the arteriotomy into the artery and placed where plaque excavation has taken place using an insertion instrument. The insertion instrument may comprise an expanding appliance, such as an arterial balloon, to expand the tubular graft from a small insertion size into a larger size contiguous with the excavated arterial wall, while at the same time permanently expanding the distal stent encased in the tubular graft.

The tubular graft insertion and expanding appliance is deactivated and removed from the artery through the arteriotomy, at which time the over length tubular graft is severed at the proximal end thereof so that the size of the tubular graft fully covers the wall of the artery which was excavated. After the proximal end of the tubular stent has been custom severed to the correct length, the expanded distal encased stent continues to hold the tubular graft in a stationary position in the artery, firmly contiguous with the adjacent arterial wall, while the proximal end is anchored permanently in its cut contiguous position against the arterial wall. This may be done in several ways. At this point, with the tubular stent graft contiguous with the adjacent arterial wall and permanently held in position at both ends, with all medical instruments and appliances removed, the surgeon will close the arteriotomy, typically with staples or sutures.

Figure 1A:
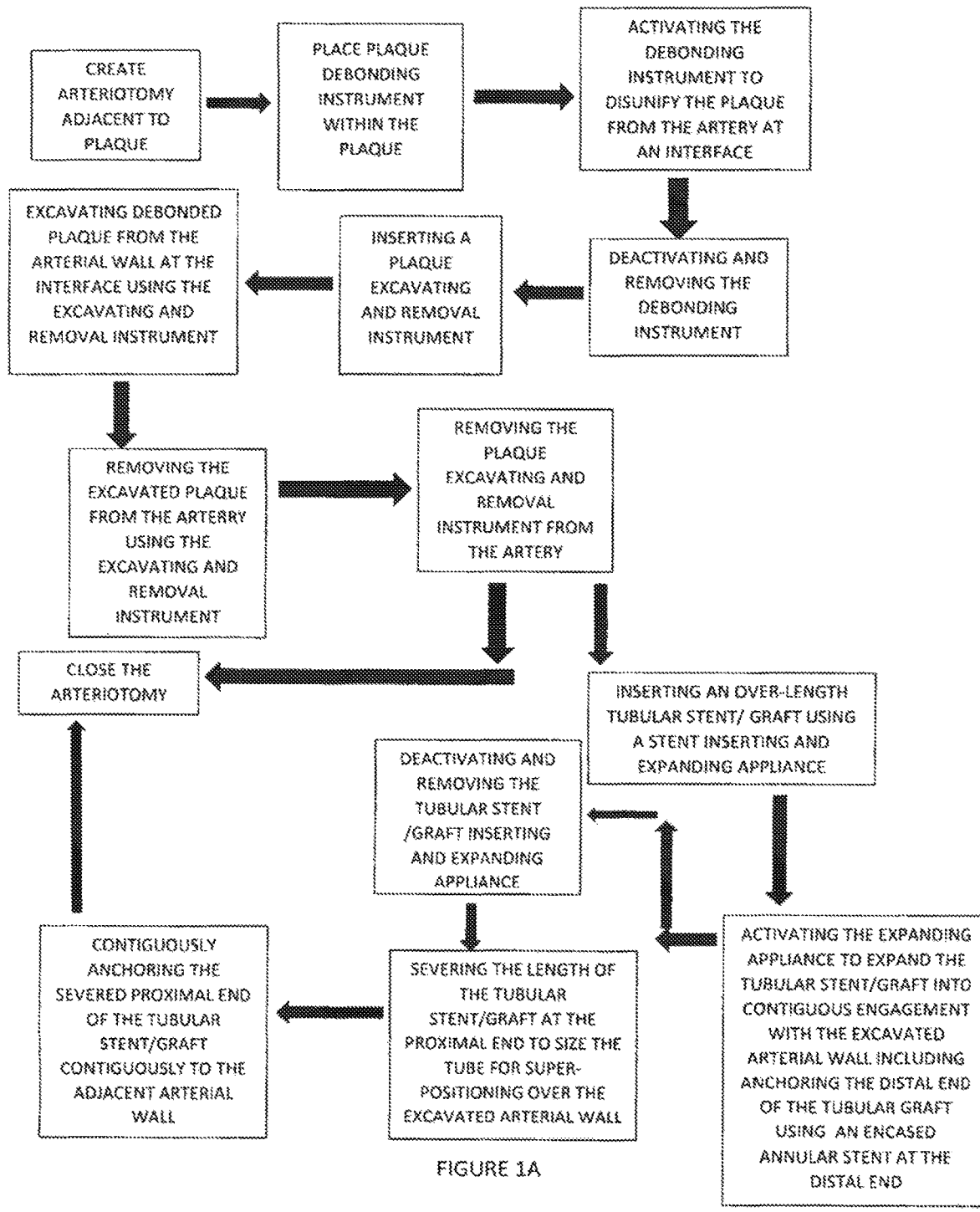
FIG. 1A is another block diagram, illustrating other aspects of the present invention.

Reference is now made to FIG. 1A, which is a second flow chart illustrating different aspects of the present invention. In the interest of brevity, FIG. 1A differs from FIG. 1 in that the same instrument is used by the surgeon for both excavating disunified plaque and removing the excavated plaque from the artery. In some embodiments of the invention, the same instrument is used to disunify, excavate and remove the plaque.

Figure 2:
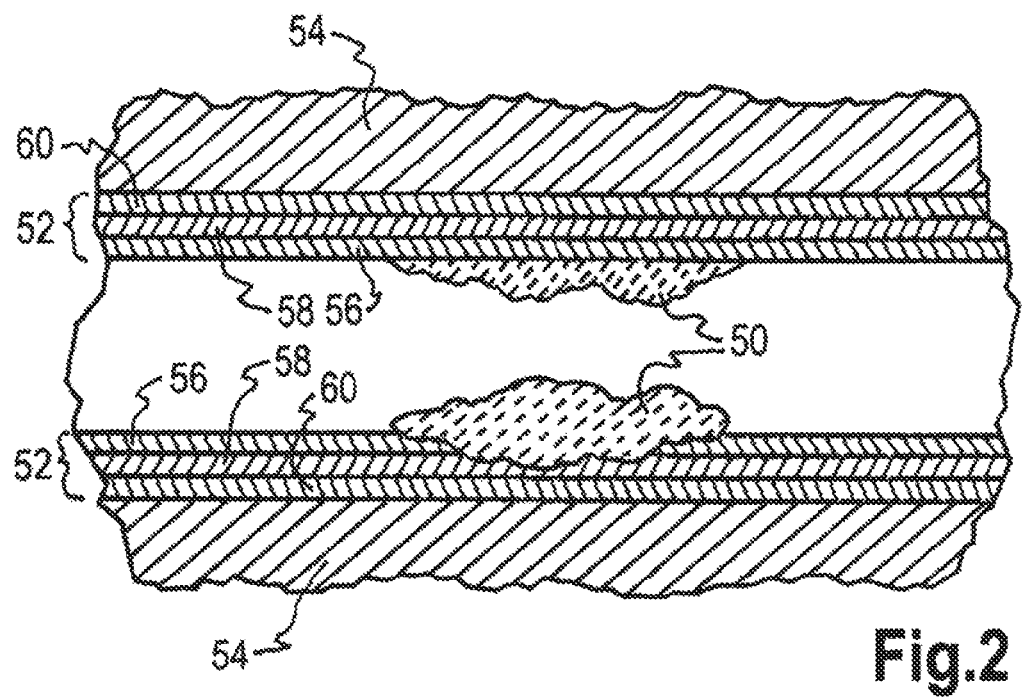
FIG. 2 is a fragmentary longitudinal cross-section of a plaque infested artery.

FIG. 2 illustrates, in fragmentary longitudinal cross-section, a plaque deposit 50 located within an artery, generally designated 52. The artery 52 is disposed within human tissue 54, as is well known. The arterial wall 52 comprises three layers, i.e. the intima 56, the media 58 and the adventitia 60. It is to be appreciated that the plaque 50 in FIG. 2 is intended to represent only one way in which plaque is found in arteries. In FIG. 2, plaque has invaded the intima and media, a common finding. Sometimes the plaque is somewhat soft and other times it can be very hard, indeed calcified. Sometimes the plaque will totally occlude an artery and at other times it will only partially occlude the artery and diagnostic x-rays and/or angiograms attempt to quantify the "percent stenosis". In either event, the parts of the human body being served by the obstructed artery is denied, in whole or in part, the benefits provided by full blood flow. This condition affects millions of Americans annually and is a major cause of death. The length of the plaque within a given artery is also a variable, at it can be short, medium or long. In some patients, some arteries accumulate plaque, while others do not.

Figure 3:
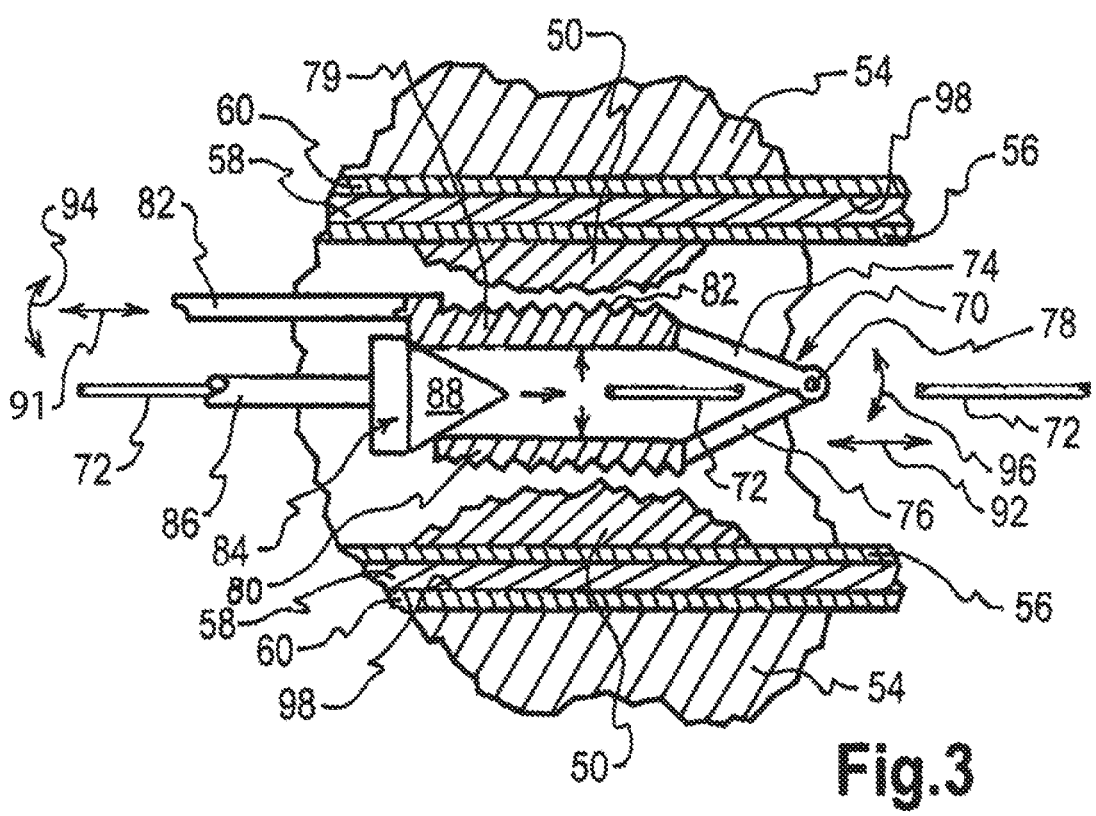
FIG. 3 is a fragmentary longitudinal cross-section of a plaque infested artery with an expandable medical gripping instrument within the plaque by which bonding at an interface between the arterial wall and the plaque is disunified.

Reference is now made to FIG. 3, which illustrates a plaque infected artery, similar to the one illustrated in FIG. 2, but with a plaque gripping instrument, generally designated 70, disposed in a location within plaque deposits 50 in the artery. The plaque gripping instrument 70 is slideably mounted on a guidewire 72 and comprises at least two oppositely spaced arms 74 and 76, hinged together for rotation at pin 78. Proximal portions 79 and 80 of the arms 74 and 76 extend from the tapered distal ends of the arms 74 and 76, and in the deactivated condition shown in FIG. 3, distal ends 79 and 80 are somewhat parallel to the axis of the artery and are shown as spaced from plaque deposits 50. Outwardly or radially directed gripping teeth or serrations 82 exist on the proximal portions 79 and 80 so that when the arms are rotated outwardly or in respect to each other around the pivot pin 78, the teeth 82 are caused to forcibly engage the adjacent plaque deposits 50. The gripping instrument 70 is positioned by the surgeon by use of a manual arm 83.

A cone-shaped spreading device 84 is advanced by a manual manipulation of shaft 86 so that the cone shaped tip 88 spreads the distal portion 79 and 80 of the arm 74 and 76 into the strong gripping relation, at teeth 82, with the plaque deposits 50.

In this position, the control rod 83 is pushed back and forth, as indicated by arrow 91, causing the plaque gripping device 70 and the plaque to move back and forth as shown by arrows 92. In addition, the control arm 83 is twisted first one way and then the other, as shown by arrows 94, causing the gripping device 72 and the plaque to rotate back and forth by arrows 96. Thus, so manipulated, the gripping device 70 attacks the pre-existing bond between the plaque and the arterial wall so as to destrengthen and disunify the bond typically along interface 98. This destrengthening and disunifying phenomena makes it easier to remove plaque from the artery in a more complete, effective and efficient way, as explained hereinafter.

Figure 4:
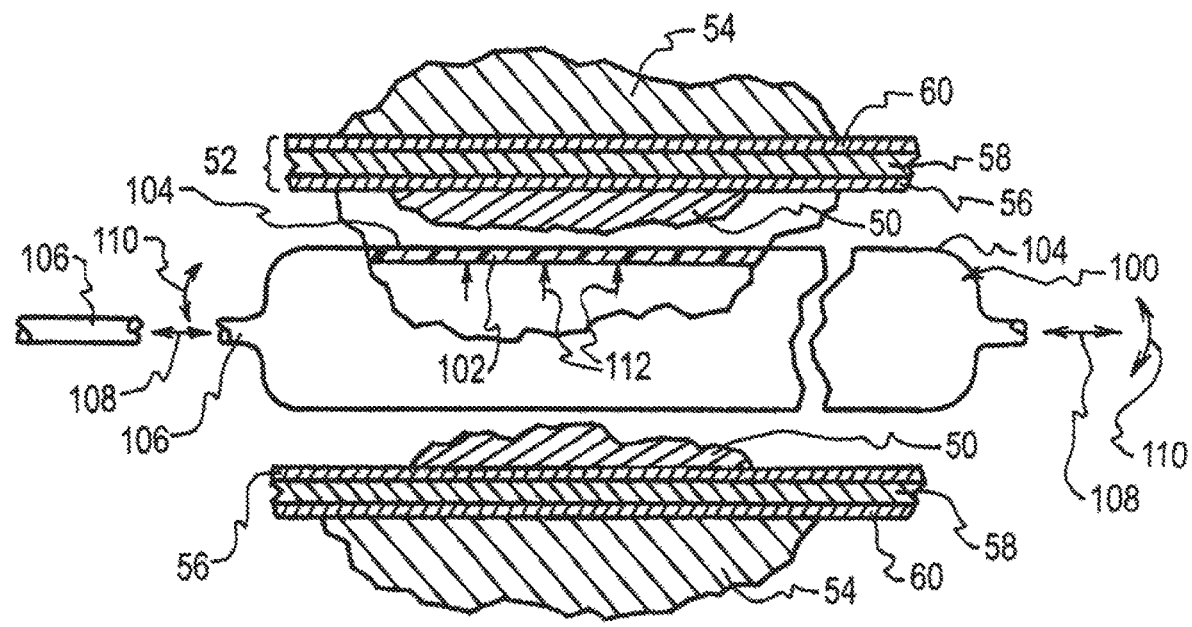
FIG. 4 is a fragmentary longitudinal cross-section of a plaque infested artery with a balloon within the plaque by which the bond between the plaque and the arterial wall is disunified prior to excavating the plaque from the arterial wall.

Another way of destrengthening and disunifying the pre-existing bond between plaque deposits 50 and the adjacent arterial wall is shown in FIG. 4. More specifically, an inelastic highly durable angioplasty balloon, generally designated 100, is introduced through the arteriotomy into a position central of plaque deposits 50, using any one of several known techniques. The wall 102 of the balloon 100 is constructed of high strength inelastic material providing a strong, abrasion resistant external surface 104 and a strong durable wall 102. The balloon 100 is inflated under pressure through a tube 106 until the surface 104 firmly and nonrotatably engages the exterior of the plaque deposits 50. At this time, the surgeon will manually manipulate the inflating stem, which must have substantial strength, back and forth, as shown by arrows 108, and in a twisting or rotational way, as indicated by arrows 110. Because of the strong grip between the surface 104 and the plaque, the axial displacement and the twisting and rotation will disunify and destrengthen the bond previously existing between the plaque and the arterial wall, making excavation of the plaque more efficient, more effective and essentially complete. All the while, the pressure 112 within the balloon 100 prevents the balloon 100 from rotating or axially displacing within the artery, except to the extent allowed by the plaque deposits 50.

Figure 5:
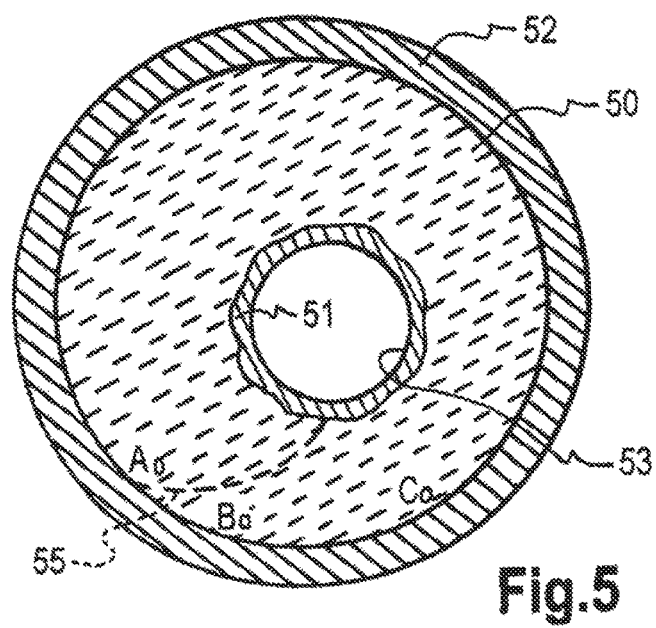
FIG. 5 is a transverse cross section through one form of plaque deposited within an artery.

The specific physical action by which this unification and destrengthening of the bond between the plaque and the arterial wall may vary considerable from case to case. As one example, reference is now made to FIGS. 5 and 6. FIG. 5 is a transverse cross section of an artery 52 in which a large amount of plaque 50 is found. The plaque 50 is shown as having a central layer 51, which defines a restricted flow path 53, shown as being somewhat eccentric to the axial center line of the artery 52. A diagrammatic line 55 is included in FIG. 5 for reference purposes, as explained more fully hereinafter.

Figure 6:
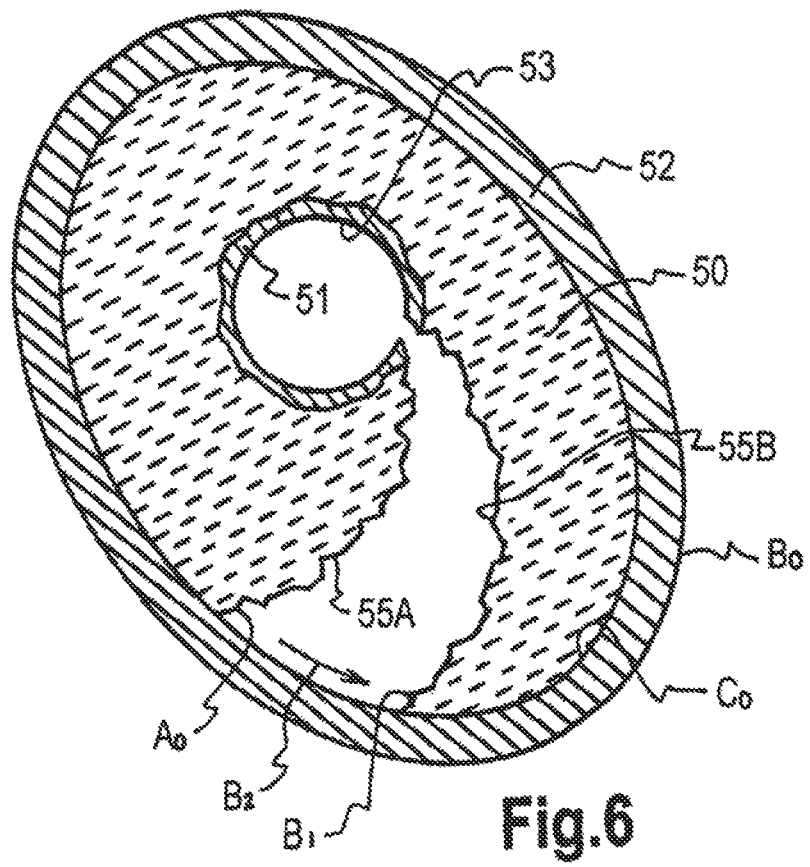
FIG. 6 is a transverse cross section of the plaque infested artery of FIG. 5 during destrengthening.

FIG. 6 illustrates one way in which a disunification and destrengthening instrument may significantly lessen the bond between the artery 52 and the plaque deposit 50. Specifically, a plaque debonding instrument, of any appropriate type, is placed within the flow path 53 and activated, as explained herein, so as to impose one or more forces directly upon the inner layer 51, which may include twisting and axial displacement to debond the interface. This debonding is illustrated in FIG. 6 for exemplary purposes only, as irregular lines 55, defining a gap therebetween. Note also, that the force or forces of the debonding instrument, tends to elongate both the arterial wall 52 and the plaque 50. In this condition, as shown in FIG. 6, plaque excavation and removal will be facilitated.

Note that prior to balloon inflation, as shown in FIG. 5, the line 55 is a line 55 is a line through the plaque where the balloon expansion will cause the plaque to separate. After balloon inflation and plaque dilation, the two sides of line 55 become separated, as denoted at 55A and 55B in FIG. 6. The way this separation is achieved is that the ends of line 55 adjacent the vessel wall, denoted as $A_0$ and $B_0$ are forced to move apart by the growth of the diameter of the balloon during expansion. In particular, $B_0$ slides along the circumference of the arterial wall from the initial position adjacent to $A_0$ position to a final position as illustrated in FIG. 6 in the direction as denoted by the arrow $B_2$. To accommodate this circumferential sliding, some portion of the plaque/wall interface is also forced by balloon pressure to slide relative to the wall, and $C_0$ is identified as the end point where the sliding separation of the plaque from the wall ends. It is to be appreciated that the point $C_0$ will vary from the treatment of one artery to another, and the more plaque filling the lumen of the artery, the greater the distance will become from A to C and thus the larger proportion of the circumference will undergo this loosening of the plaque.

Figure 7:
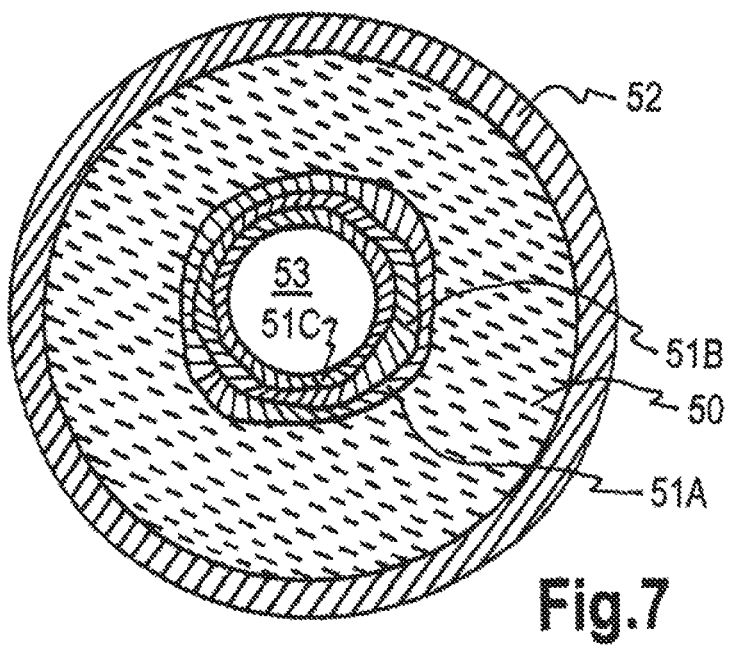
FIG. 7 is a transverse cross-section of another plaque infested artery, layers of plaque.

Reference is now made to FIGS. 7-10, to illustrate and describe the somewhat different mechanism by which plaque may be debonded from an artery preparatory to excavating and removing the disunified plaque. With the specific reference to FIG. 7, an artery 52, a body of plaque 50 comprising annular layers of calcified or hard plaque 51A, 51B, and 51C are illustrated. Innermost plaque layer 51C defines a constricted blood flow path 53. FIG. 7 depicts plaque 50 outside these inner layers. However, plaque may be composed of additional thin layers.

Figure 8:
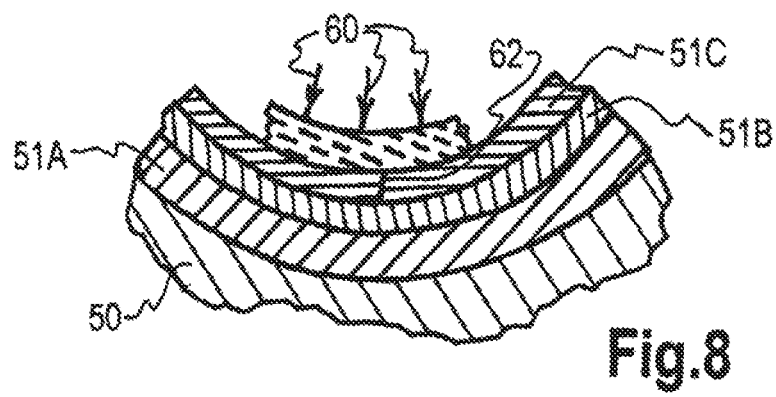
FIG. 8-10 are transverse cross-sections of a plaque infested artery, showing layers of plaque being disunified.
Figure 9:
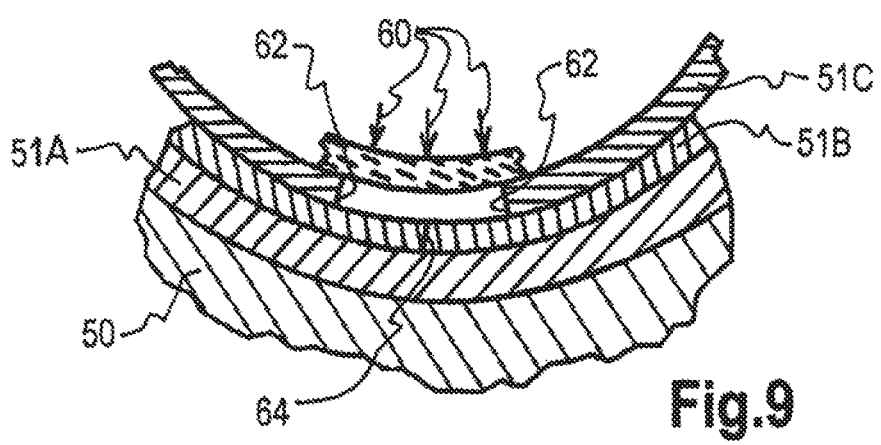
Figure 10:
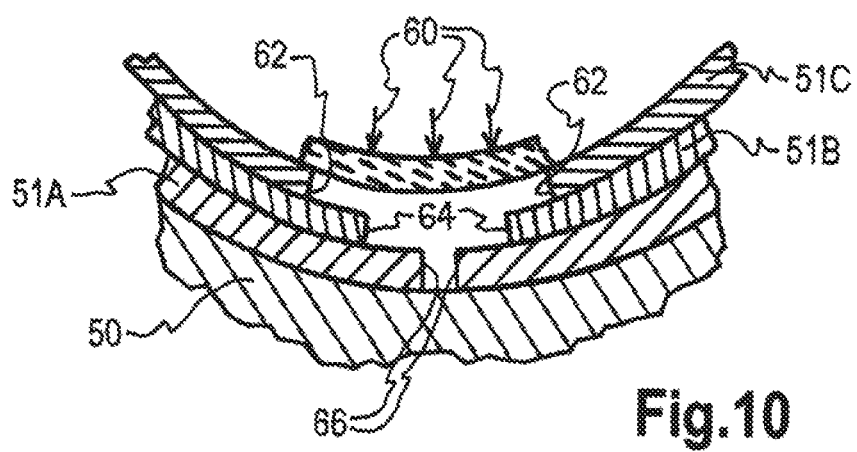

FIGS. 8-10 illustrate, in sequence, one example of how the operation of a suitable debonding instrument, creates forces (illustrated in FIGS. 8-10 by arrows 60), which forcibly impact upon plaque layers 51A, 51B, and 51C. The debonding forces 60, which may be of any type, including but not limited to axial to and fro placement of the debonding instrument and twisting of the debonding instrument, and/or radial dilation via an inelastic balloon of a tapered device, a innermost such that layer 51 C is cracked at the site 62 (FIG. 8) and thereafter separates to create a space at site 62, while also creating a fracture 64 in layer 51B. FIG. 9. With continued application of debonding forces 60, the facture line at site 64 separates, as shown in FIG. 10, to create a gap in plaque layer 51B, while also fracturing plaque layer 51 A and creating a gap at site 66.

Figure 37:
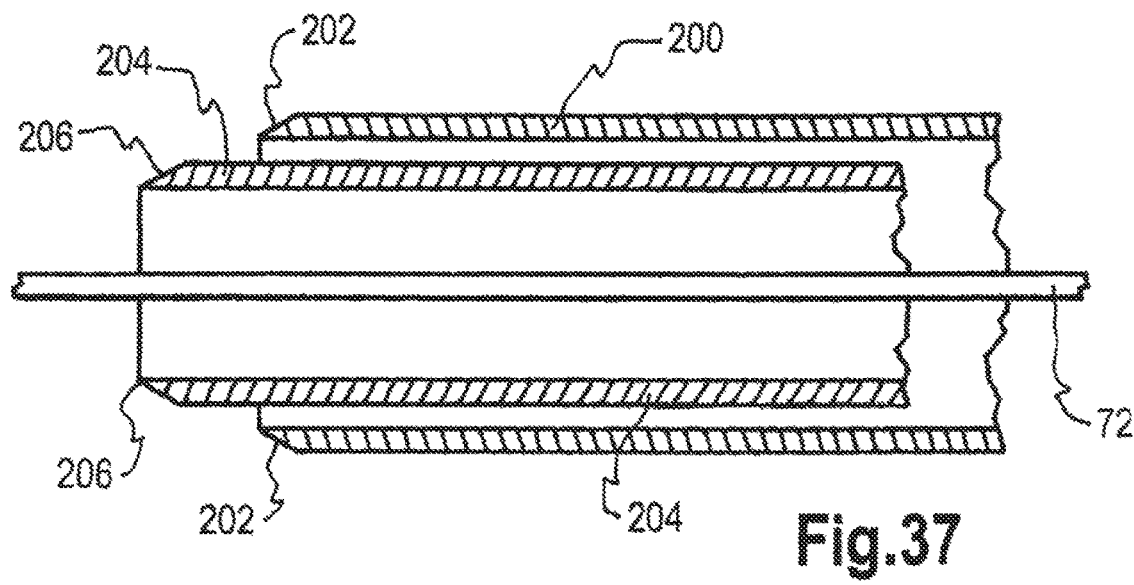
FIGS. 37-38 are fragmentary cross sections depicting use of multiple concentric sheaths to stretch an arterial wall to disunify the plaque.
Figure 38:
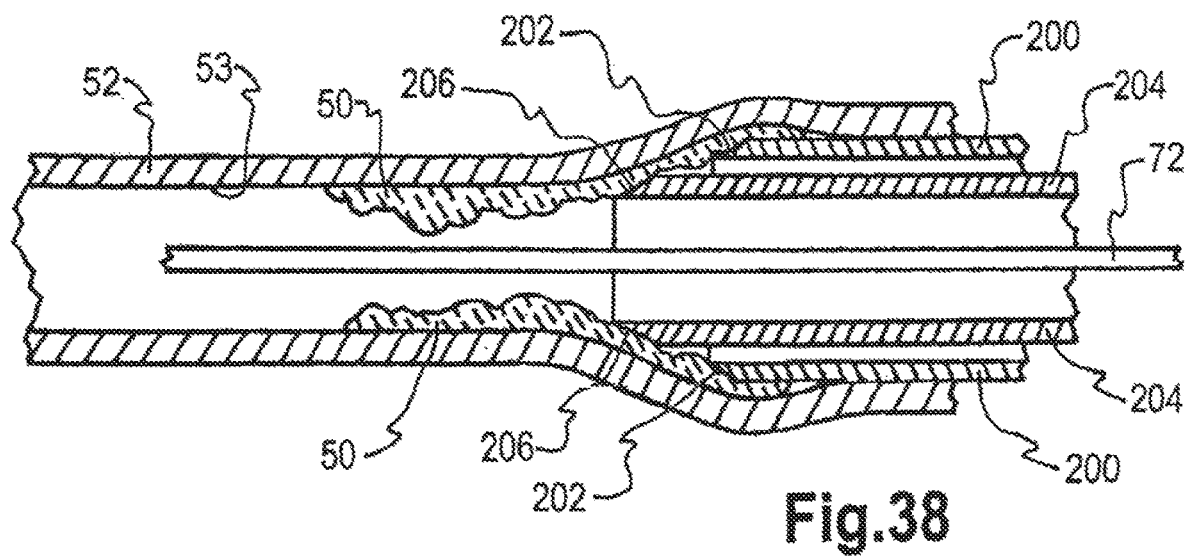

Debonding forces may also be generated by a device within lumen 53 that dilates the vessel in an outward direction relative to lumen 53. One such device may take the form of an angioplasty balloon. Another such device may take the form of a set of two dottering sheaths as shown in FIG. 37-38. In such a set of sheaths, an inner sheath closely fits around the guidewire, and one or more successively larger sheaths may be advanced, each closely fitting around the next-smaller sheath inside. Such sheaths may be used to dilate plaque in a vessel, as illustrated in FIG. 38. The principle is in FIG. 38, where the first inner sheath 200 is advanced through the plaque. As the tapered leading edge 202 of the sheath 200 is advanced over the guidewire 72, the plaque 50 is forced to dilate outward, and forces are generated which, initiate the separation of layers of plaque, as shown in FIG. 6. These forces can produce the spiral separation described earlier, which can thus produce disunification of the plaque from the vessel wall as desired as an initial step leading to plaque excavation and removal. One sheath can produce a given amount of dilatational force, and as subsequent, larger diameter dottering sheaths are advanced over the first sheath, the force and amount of disunification can thereby be increased, leading to a larger portion of the circumference of the plaque being disunified from the vessel wall.

Using dottering sheaths offers certain advantages compared to other methods. It allows for gradual expansion force to be applied by each successively larger diameter sheath. This reduces or eliminates the risk of damage to tissues and/or vessels that may occur by the use of rotational or oscillatory forces via other devices, although such other devices may apply more energy and thus produce more disunification.

But dottering sheaths have some disadvantages. The long length of the sheath is in contact with the plaque and this long friction contact surface may impede the advancement of the sheath. In long plaque occluded sections of the vessel, advancement may become impossible, thus limiting the patients who can be treated. Also the device is advanced by a series of small advances, then the device halts, is regrasped, and further advancement occurs. Each time the device halts and then is readvanced, the operator must overcome the static friction between the device and the plaque. It is familiar to engineers that static friction is greater than dynamic friction, such that it has been given its own name, "stiction", as a contraction of static and friction. The operator typically during advancement rotates the device first clockwise then counterclockwise during advancement, this movement increasing the degree of dynamic or moving friction that comes into play, which is a lower level of friction. This hand-powered rotation of the device reduces the friction and makes the device easier to advance.

Figure 34:
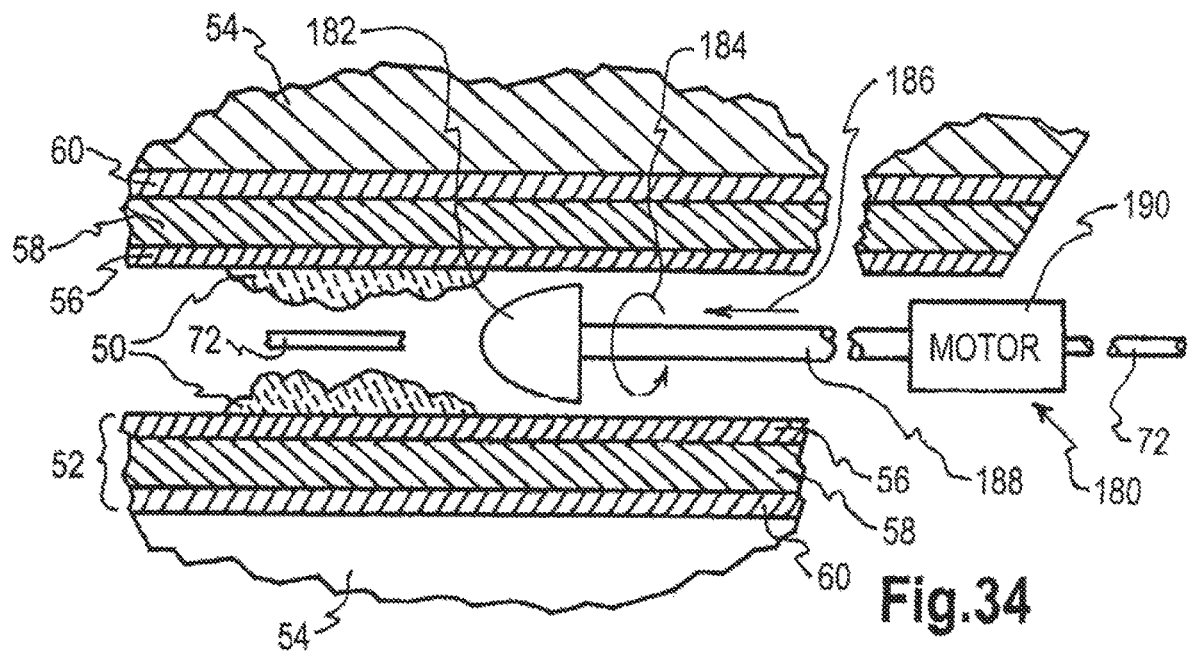
FIGS. 34-36 are fragmentary cross sections depicting a plaque excavating instrument which is motor driven.
Figure 35:
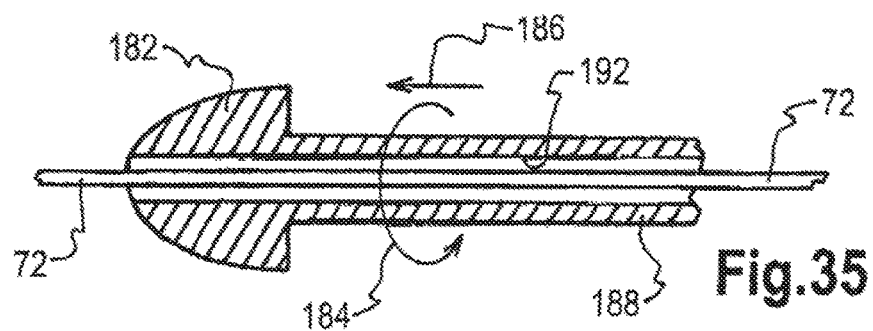
Figure 36:
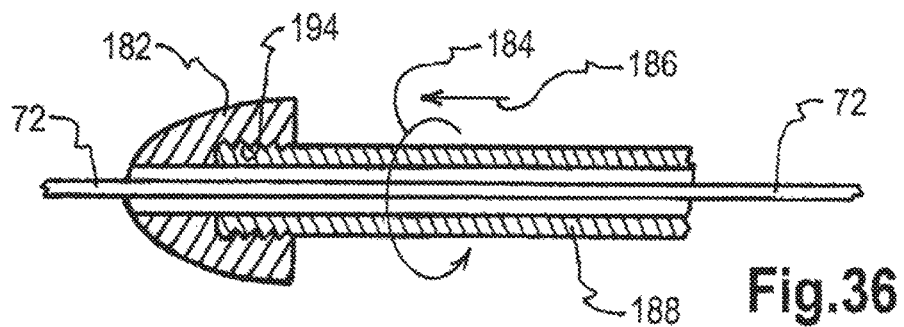
Figure 39:
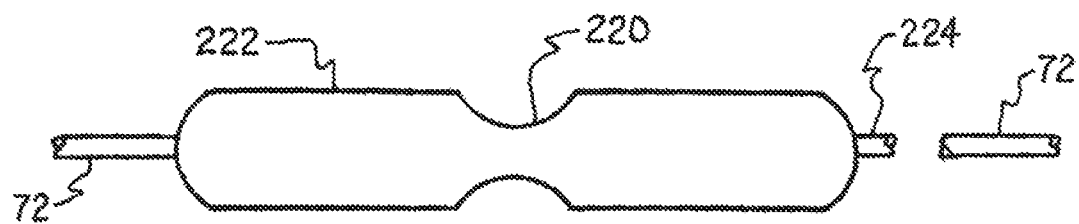
FIG. 39 is a representation of a balloon used to locate plaque in an artery.
Figure 40:
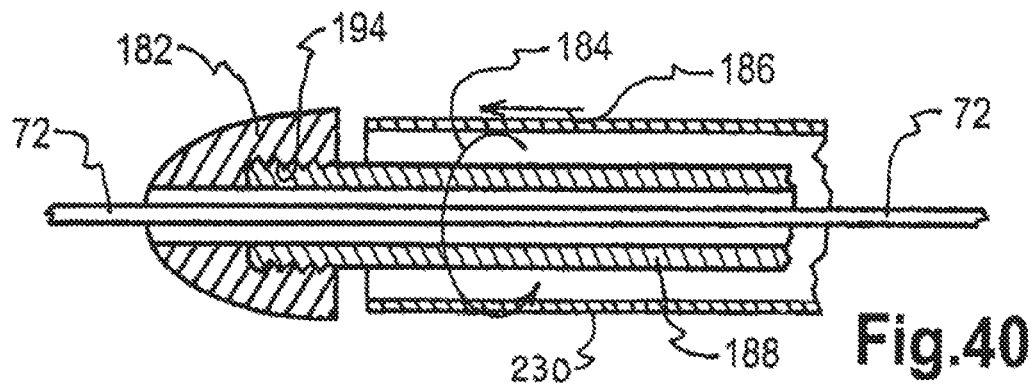
FIG. 40 is a longitudinal cross section of the instrument of FIG. 36 surrounded by a stationary tube.

A device which solves a number of problems in disunifying plaque from the vessel wall by use of dilation, including reducing the friction of using dottering sheaths both by shortening the length of the larger diameter shaft in contact with the tight plaque, and also maintaining the device in constant motion so as to always be in a state of low, dynamic friction, is illustrated in FIGS. 34-36. A motor drive located in the device handle rotates an inner shaft 188 connected to a hard, rotating tip 182, which may be one of a series of exchangeable tips, such as tip 182 illustrated in FIG. 36, which is composed of rigid material such as thermoplastic or surgical grade stainless steel. Compare FIGS. 35 and 36. FIG. 40 shows a stationary protective tube 230 surrounding the rotating shaft 188. The short length of the tip eliminates the friction resistance produced by the long length of the shaft of dottering sheath. The motor drive keeps the tapered tip in a constant rotation, thus constantly experiencing the lower dynamic friction as opposed to the higher static friction. The hard tip, when advanced through an area of a vessel narrowed by plaque, must at some point dilate the lumen to the size of the largest diameter of the tapered tip. The tip simply cannot pass through the plaque any other way than by, at least momentarily, dilating the lumen to the size of the tip. This solves a problem with dilation via balloon, where sometimes a very tight plaque stenosis cannot be dilated even by the full pressure of a modern balloon catheter. The angiographic sign of this is referred to as "wasp waisting" and is at site 220 illustrated in FIG. 39. Since the balloon 222 is inflated at entry site 224 using radiopaque contrast media, the balloon 222 is clearly visible on angiography, as is the guidewire 72 and the shaft 224 of the balloon. The wasp waist sign 220 clearly indicates that balloon has failed to fully inflate at a tight stenosis, thus producing incomplete dilation and as a consequence, incomplete disunification.

Further details of the tip of the device are illustrated in FIG. 40. In this embodiment, the inner rotating shaft 188, which is threadedly connected to the tapered tip 182 is surrounded by an outer, non-rotating shaft 230 connected to the housing of the motor drive (FIG. 34). This arrangement protects the tissues and structures of the vessel from accidental damage by the rotating shaft 188 for instance, for example, if tissue were to become entangled with the rotating shaft leading to damage of the tissue. The tapered tip 182 is screwed onto the rotating shaft via the threads 194, which permits exchange of tapered tips of different sizes, 182 smaller followed by successively larger tips, for instance.

Figure 11:
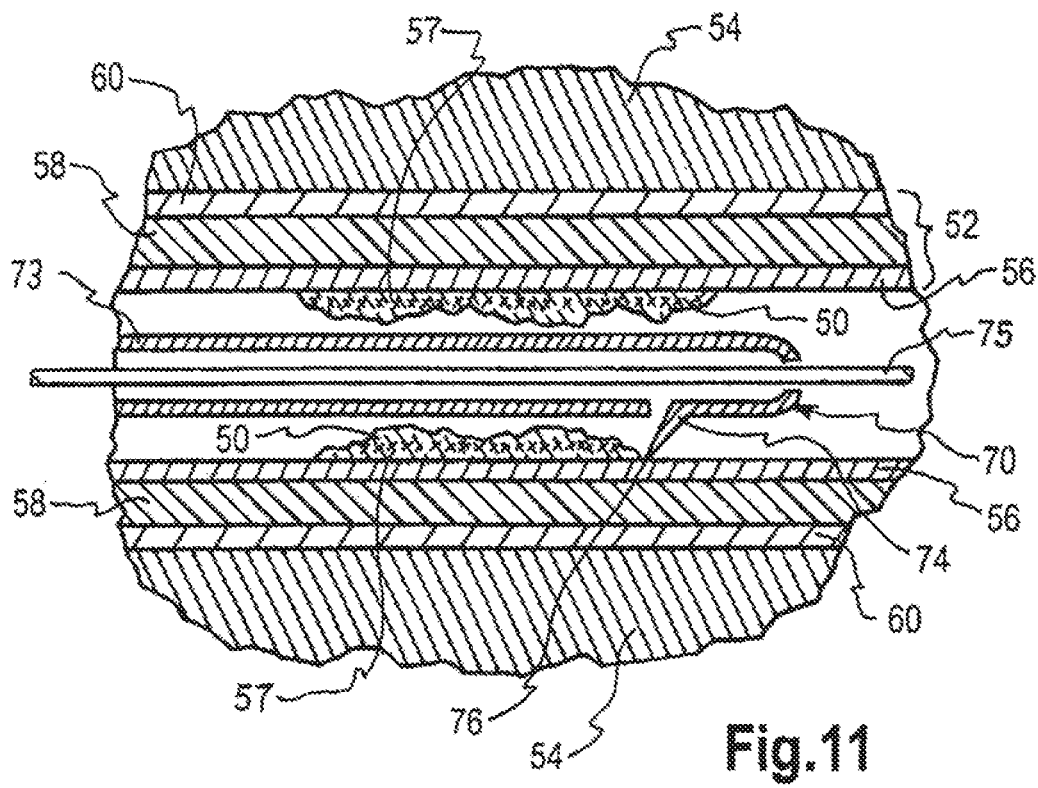
FIG. 11 is a fragmentary longitudinal cross section of an artery containing a failed stent, illustrating use of a reverse barb instrument to disunify a bond between the plaque and the arterial wall.

Reference is now made to FIG. 11 which illustrates a further medical instrument, shown as being disposed within restenotic plaque deposits 50 in an artery 52, having a failed encased stent 57. The plaque may be debonded, disunified and destrengthened at an interface between the plaque and the arterial wall using the instrument of FIG. 11. The instrument of FIG. 11, generally designated 70, comprises a hollow housing 73, the proximal end of which is available to the surgeon for manual manipulation adjacent to the site of an arteriotomy. The instrument 70 is illustrated as being slideably mounted on a guidewire 75, by which the instrument 70 is moved while essentially being retained central of the artery during the debonding procedure. Near the distal end is a plaque-engaging outwardly directed barb 74 having a tip 76. The barb 74 is somewhat proximally directed and is essentially rigid and durable, as is the hollow tube 73 to which the barb 74 is connected. By placing the barb 74 distal of the plaque deposits 50, the surgeon is able to manipulate the housing 73 adjacent to the arteriotomy, both rearwardly in a somewhat axial direction and rotationally around the distal edge of the deposits of plaque 50, so as to disunify and destrengthen the bond between the plaque 50 and the arterial wall 52. By repeating this manual procedure, as many times as appropriate, the bond is further disunified and destrengthened. While restontic plaque is shown only in FIG. 11, it is to be appreciated that the plaque deposit shown in the other figures can be stenotic and/or restenotic plaque, with or without a failed stent from a prior treatment.

All treatments for arteries occluded by plaque are subject to restenosis, including balloon angioplasty, drue coated balloon angioplasty, atherectomy, endarterectomy and stent placement. FIG. 11 illustrates a stent which was previously placed. Subsequently restenosis caused plaque to be deposited in the artery in areas proximal and distal to the stent and also inside the stent itself producing a total occlusion of the stent. In one clinical application of the devices and methods described elsewhere herein, plaque is disunified from the arterial wall using one of the ring type disunification and debonding devices shown in more detail in FIGS. 14 and 15 and elsewhere herein.

FIG. 11 illustrates restenotic plaque and the occluded stent in the process of being removed from the artery using the excavating device 70, as explained elsewhere in this application.

For some patients, the utilization of a debonding instrument, such as those shown and described in connection with FIGS. 3, 4 and 11 is medically satisfactory, in anticipation of excavation and removal of plaque at the debonded interface between the arterial wall and the plaque, use of a single instrument to both debond and excavate has advantages with some patients, as explained herein in greater detail.

Figure 12:
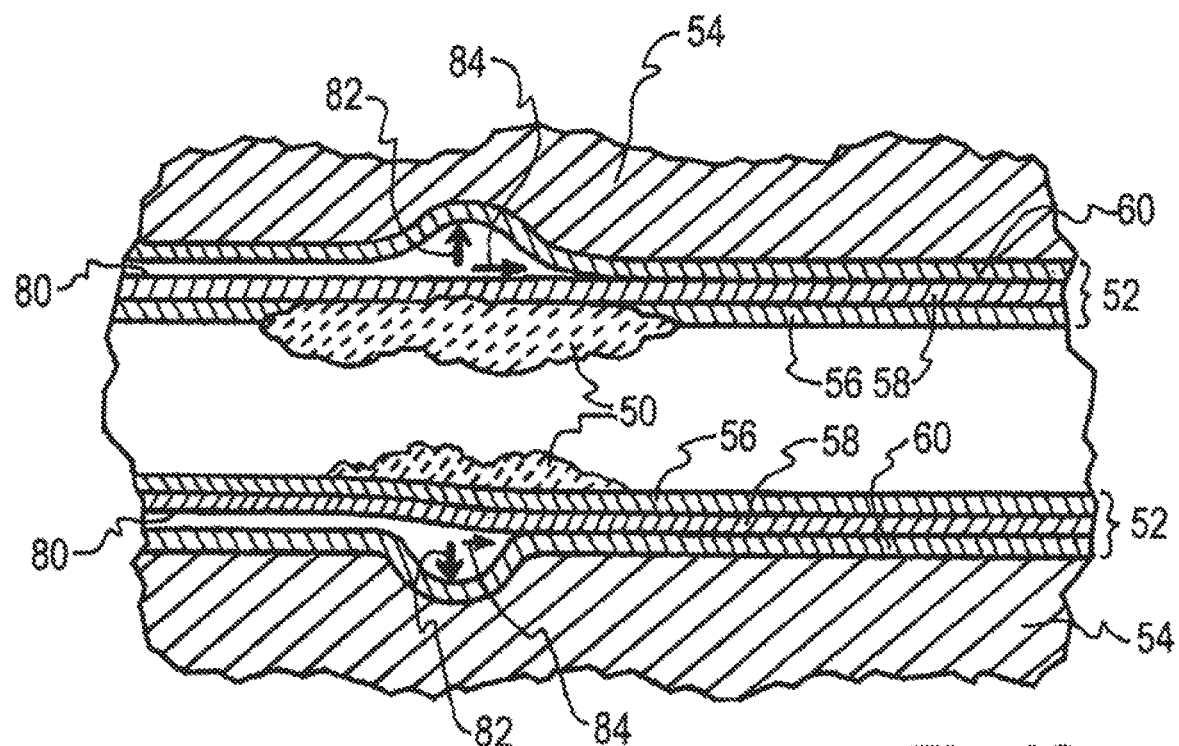
FIG. 12 is a fragmentary longitudinal cross-section of an artery, diagrammatically illustrating forces caused by a medical instrument to stretch the arterial wall outwardly away from a plaque to both disunify a bond between the plaque and the arterial wall and to excavate the plaque from the artery along an interface between the retained arterial wall and the plaque being removed.
Figure 13:
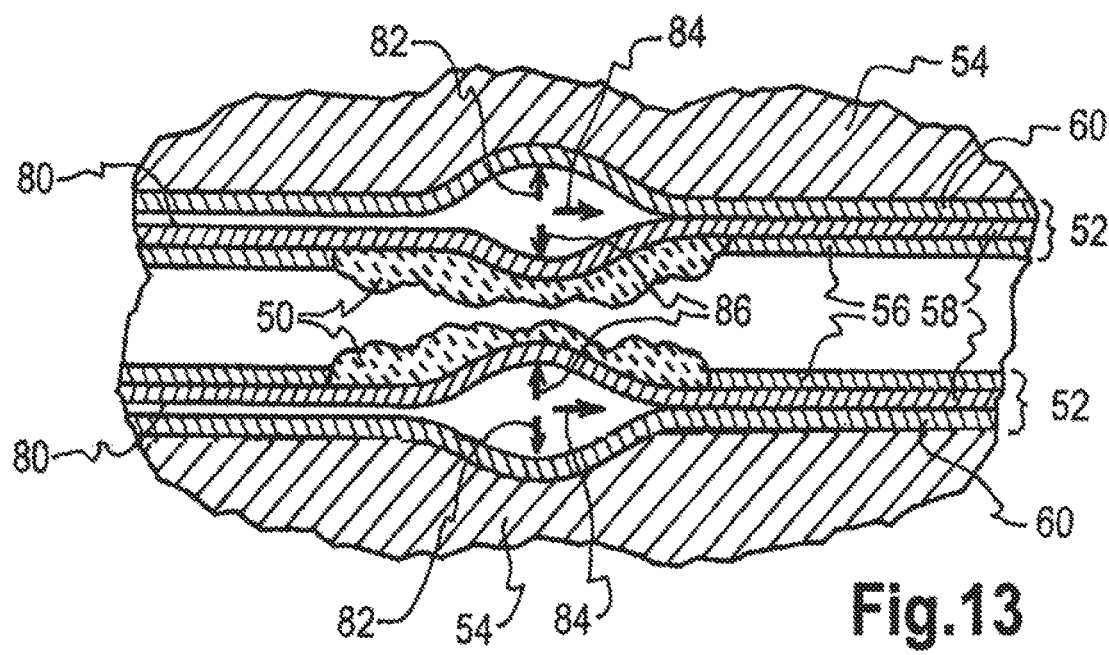
FIG. 13 is a longitudinal cross section similar to FIG. 12, further illustrating an additional inward force caused by a medical instrument to disunify and excavate.

FIGS. 12 and 13 illustrate two presently preferred methods by which a single instrument can both disunify a bond between the plaque and the arterial wall and also excavate the disunified plaque from the residual arterial wall. FIGS. 12 and 13 diagrammatically disclose the forces used in these two presently preferred methods. Without regard to the particular instrument used, FIG. 12 illustrates that the instrument of choice is inserted between the adventitia and media layers of the artery in such a way as to materially stretch the adventitia layer outwardly away from the media layer and the interior plaque itself, thereby creating an annular gap 80 at an proximal of the instrument itself. The outward stretching of the adventitia layer is diagrammatically illustrated by arrows 82 in FIG. 12. Also, in FIG. 12, the media layer is illustrated as remaining essentially annular. The debonding and excavating instrument is also displaced in a distal direction, as illustrated by arrows 82 thereby excavating the plaque 50, the media layer 58 and the intima layer 56 away from the adventitia layer with significant accuracy and greater ease, given the partial debonding caused by force 82. The advancement of the debonding and excavating instrument between the adventitia and intima layers is diagrammatically illustrated in FIG. 12 by arrow 84.

With reference to FIG. 13, a second procedure is illustrated by which the plaque is more effectively and efficiently removed from an artery using debonding and excavating instrument as described in FIG. 12 whereby the FIG. 13 instrument not only implements forces 82 and 84, but also imposes a force 86 on the media layer so as to deflect it inwardly and the plaque as well.

Figure 14:
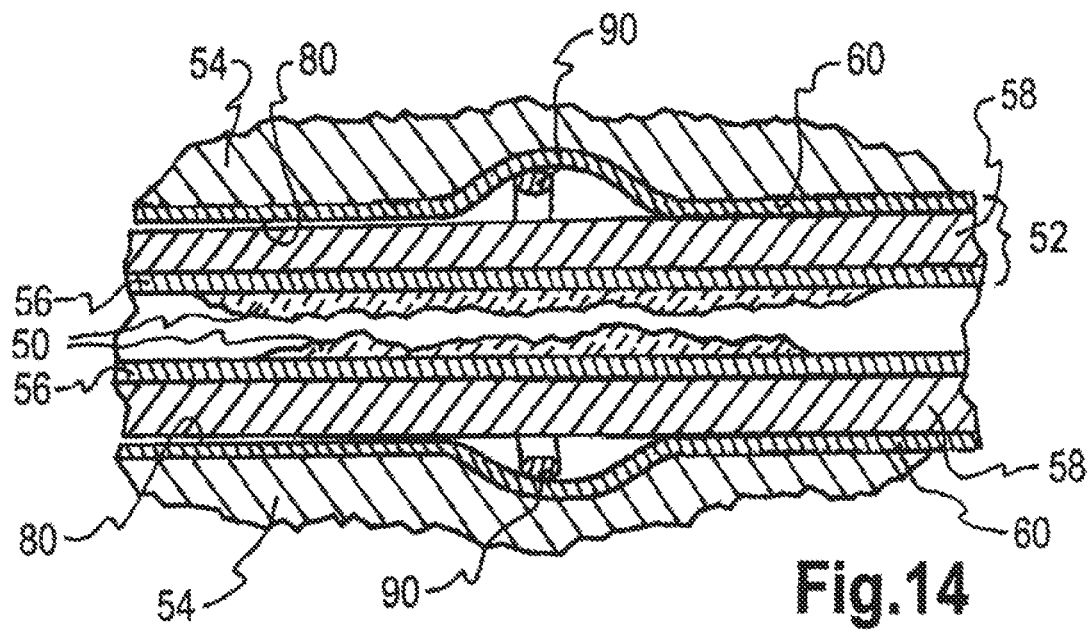
FIGS. 14 and 15 are fragmentary longitudinally cross sections of an artery showing use of an expandable loop, in accordance with principles of the present invention, to both disunify a bond between plaque and an arterial wall and to excavate the disunified plaque from the wall.
Figure 15:
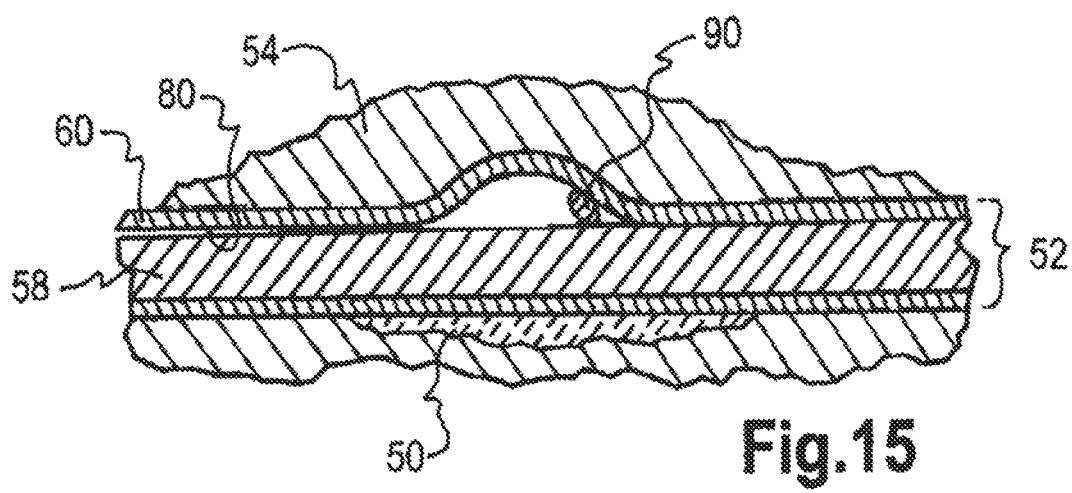

Reference is now made to FIGS. 14 and 15, showing utilization of an adjustable (enlargeable) ring stripper by which plaque 50, in artery 52 is both disunified at the naturally occurring bond at an interface 80 between the arterial wall at the adventitia 60 in respect to the media 58 and excavated. FIGS. 14 and 15 show only the adjustable loop 90 itself and does not illustrate control structure, by which the loop 90 is manipulated by a surgeon through to an arteriotomy.

More specifically, the surgeon will manipulate the loop 90 so that it is displaced down the interface 80 between the adventitia 60 and the media 58, while at the same time stretching a portion of the adventitia 60 outwardly so as to exert a pull away from the media 58, the intima 56 and the plaque 50. This is done in a progressive way with the loop 90 being advanced by the surgeon along the interface 80. Not only does the loop 90 stretch the adventitia, as shown in FIG. 14, but also excavates the media 58, the intima 56 and the plaque 50 from the adventitia 60, as shown in FIG. 15. The surgeon typically relies on fluoroscope—type technology to visually determine correct manipulation of instruments in the artery.

Figure 16:
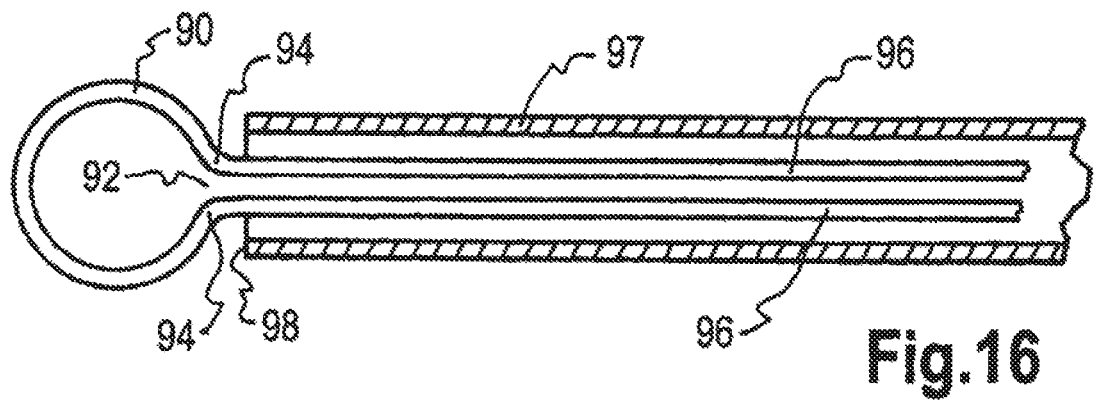
FIG. 16 is a plan view showing, partially in cross-section, an expandable loop the respective ends of which are joined to spaced wires placed in a tubular sheath.
Figure 17:
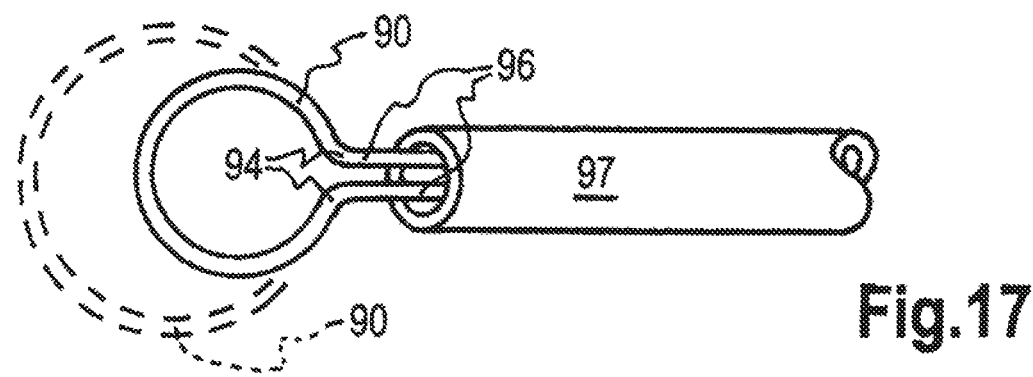
FIG. 17 is an enlarged fragmentary plan view of the exposed loop of FIG. 16.
Figure 18:
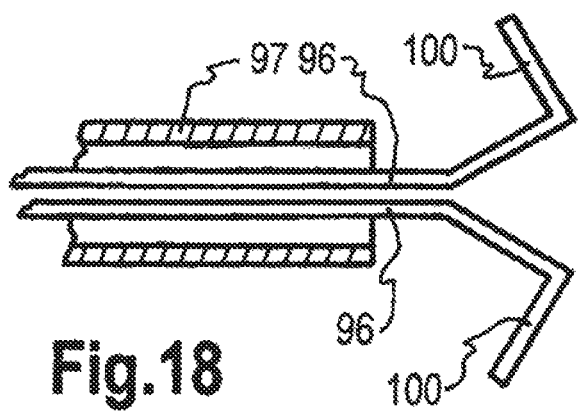
FIG. 18 is a diagram of a control by which the wires, respectively attached to the ends of the loop shown in FIG. 16, are individually manipulated to enlarge the size of the loop.
Figure 22:
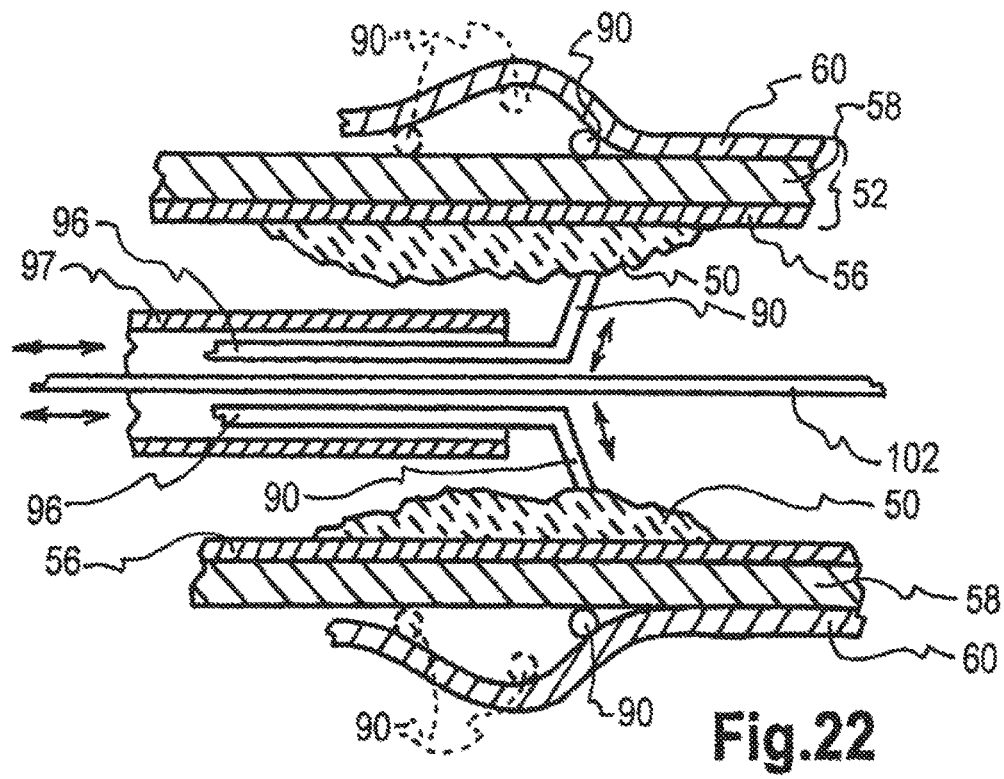
FIG. 22 is a fragmentary longitudinal cross-sectional view of a plaque infested artery with an adjustable loop being used to both outwardly stretch the residual arterial wall away from the plaque and to excavate the plaque from the residual arterial wall.

Reference is now made to FIGS. 16-18, which illustrates one version of the expandable (adjustable) loop 90 having a space 92, between two ends 94. Each loop end 94 is connected to a loop-control wire 96, the two wires being shown as essentially parallel, but spaced one from the other. The wires 96 are contained within a tubular sheath 97, the distal end 98 of which is located immediately proximal of the loop ends 94. Thus, the surgeon is able to manipulate the wires 96 separately or together, using handles 100 (FIG. 18). The handles 100 and proximal ends of the wires 96 extend beyond the arteriotomy a reasonable distance to allow facile independent and collective manipulation of the wires 96, to selectively enlarge the loop from its initial size, as shown in FIG. 16 and in solid lines in FIG. 17 to an enlarged loop, shown in dotted lines in FIG. 17. The wires are also used to reduce the size of the loop 90 as required. This size adjustment in the loop 90 accommodates expansion, as shown in FIG. 14, to stretch the adventitia 60 away from the media 58 and to reduce the size of the loop 90 somewhat for purposes of excavating along the interface 80, as shown in FIG. 15. This manipulation using wires 96 to enlarge the loop 90 is shown as a series of progressions in FIG. 22. In FIG. 22, the sheath 97, the wires 96 and the loop 90 are illustrated as being slideably disposed on a guide wire 102 to retain essentially concentricity within the artery itself.

Figure 19:
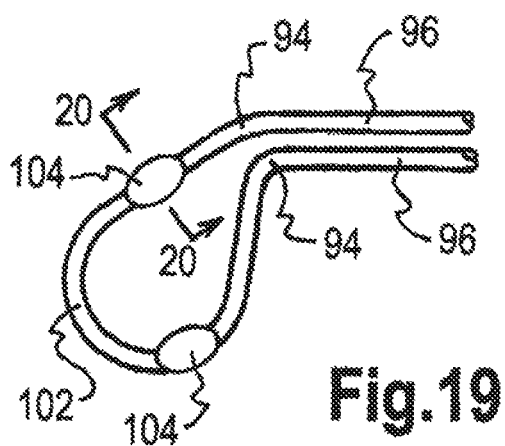
FIG. 19 is a plan view of a second adjustable loop constructed in combination with two expandable balloons for enlarging the size of the loop.
Figure 20:
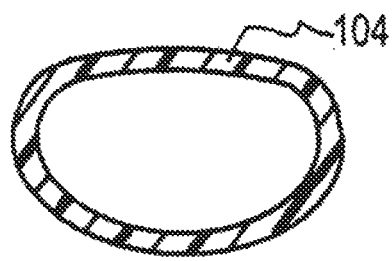
FIG. 20 is a cross-section taken along lines 20-20 of FIG. 19, with the illustrated balloon deflated.
Figure 21:
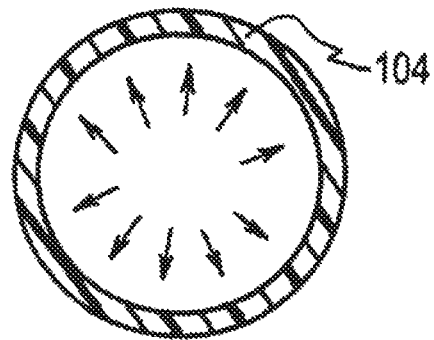
FIG. 21 is a transverse cross-section similar to FIG. 20, with the illustrated balloon inflated.

Reference is now made to FIGS. 19-21, which illustrates another version of an adjustable (expandable) loop 102, with the tubular sheath 97 and a balloon inflating and deflating tube removed for ease of presentation. More specifically, in reference to FIG. 19, two expandable balloons 104 form part of the loop 102, such that when expanded from the deflated position of FIG. 20 to the inflated position of FIG. 21, the size of the loop 102 is enlarged. The extent to which the balloons 104 are inflated and the selectably deflated by the surgeon will determine the size of the loop 102. Thus, the loop 102 will function essentially as loop 90 in FIGS. 14, 15 and 22.

Figure 20A:
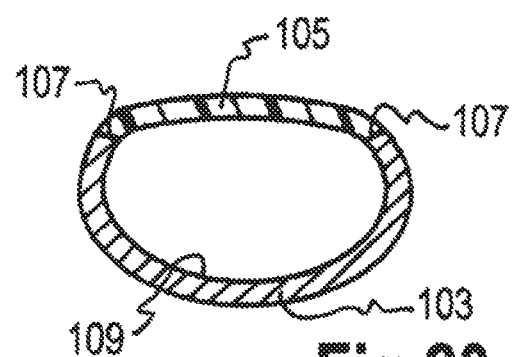
FIG. 20A is a transverse cross section similar to FIG. 20, but wherein part of the balloon section comprises a solid arcuate part and a balloon part.
Figure 21A:
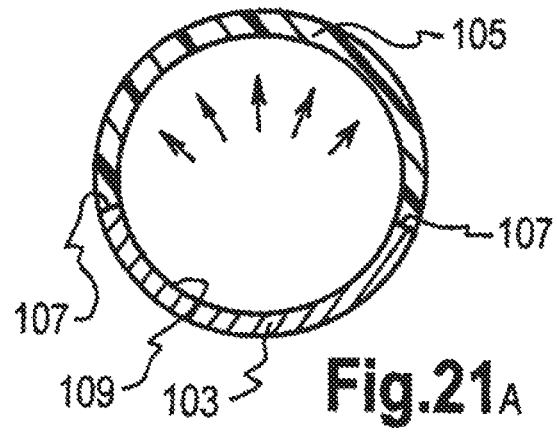
FIG. 21A is a transverse cross section of the balloon section of FIG. 20A, with the balloon inflated.

In lieu of one or more full balloons 104 as part of the loop 102, one or more partial balloons may be used over a semi-circular solid parts of the loop, as shown in FIGS. 20A and 21A. More specification, the loop 102, at one or more sites 103, comprise a U-shape, as shown in FIGS. 20A and 21A, leaving an open concavity 109. A convex partial balloon segment 105 is firmly sealed to the edges of the concavities 103 at sties 107 so as to have a smaller outward dimension when deflated, as shown in FIG. 20A. When inflated, the partial balloon segment or segments outwardly enlarge causing the overall radial size of the loop to be enlarged to accommodate the use shown and described in respect to FIGS. 14 and 15. The surgeon selectively controls the degree of inflation, such that the adjustable loop 102 can both disunify, as shown in FIG. 14, and excavate, as shown in FIG. 15.

Figure 23:
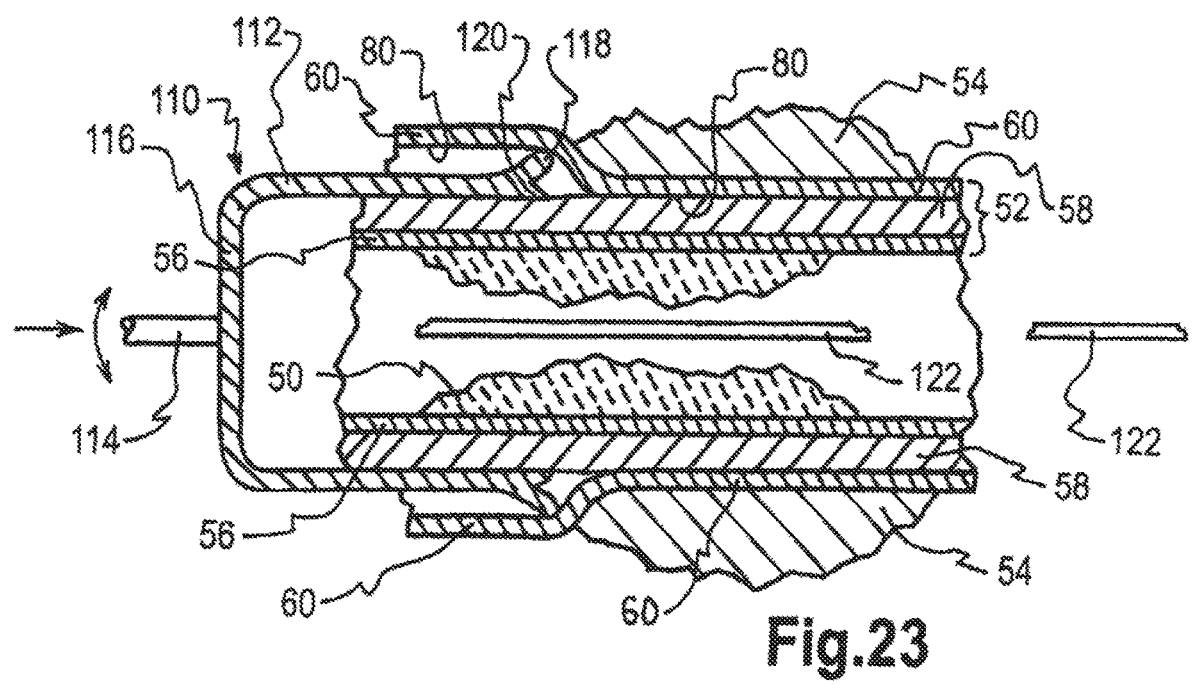
FIG. 23 is a fragmentary longitudinal cross-sectional view of a plaque infested artery showing an annular stretching and excavating instrument used to both stretch the arterial away from plaque and to excavate the plaque from the arterial wall.

In reference to FIG. 23, an annular or cup-shaped disunifying and excavating instrument, generally designated 110, is illustrated. Instrument 110 comprises a cup-shaped or annular disunifier and excavator 112, mounted upon a stem 114, the proximal end of which extends beyond an arteriotomy for manipulation by the surgeon. The cup-shaped instrument 112 comprises a base wall 116 to which the stem 114 is securely and non-rotatably attached. At the distal end of wall 112, is disposed an integral stretching annular element 118 and a cutting annular element 120. In order to stretch the adventitia to disunify the stretching annular element 118 is disposed somewhat forward of the cutting annular element 120. Thus, as the stretching annular element 118 forces the adventitia outward during rotation of the instrument 110, the cutting annular element 120 excavates the adventitia at interface 80. To achieve general concentricity between the artery and the instrument 110, the instrument 110 is preferably slideably mounted on a guide wire 122.

The present invention embraces a multi-purpose single instrument is used to disunify, excavate and remove excavated plaque from an artery. Specifically, in reference to FIG. 24, which illustrates in longitudinal cross-section a plaque infested artery and use of a single barbed instrument, generally designated 130. The instrument 130 comprises a proximally directed and outwardly extending barb 132, having a rounded tip 134. The instrument comprises a distal aperture 136 through which a guidewire 138 slideably extends, so as to retain the instrument 130 essentially concentric within the artery while allowing the instrument 130 to move both along the axis of the artery and rotationally, for purposes to be explained. The radial distance to which the tip 134 extends beyond the tubular portion 140 is selected to be slightly larger than the diameter at interface 80. Thus, as the surgeon moves the reverse barb 132 back and forth and rotationally, the tip 134 will outwardly stretch the adventitia 60, as illustrated at site 142 in FIG. 24. This stretching destrengthens and disunifies a preexisting bond between the arterial wall and the plaque infested region of the artery.

The reverse barb 132 is positioned initially distal of the plaque deposit to be treated and the barb 132 is generally advanced from a distal position to a proximal position. As this occurs, there is an accordion effect created in the media 58, the intima 60 and the plaque 50, as shown in FIG. 24. Specifically, the intima 56 is essentially fan folded, as shown at site 144, as is the plaque 50, as shown at site 146. As this accordion effect continues, the plaque, the intima and the media are not only excavated from the adventitia but are progressively displaced toward and out the arteriotomy. As the instrument 130 is removed through the arteriotomy, so too is the last of the excavated plaque, the excavated intima and the excavated media. Thus, the instrument 130 disunifies, excavates and removes, with accuracy, completeness and efficiency.

Reference is now made to FIG. 25, which shows an instrument 150 similar to the above-described instrument 130 of FIG. 24, but having two reverse barbs, rather than one. Instrument 150, to the extent it is the same as instrument 130, has been so designated with the same numerals and no significant repeat description is needed. However, the instrument 150 comprises a second reverse barb 152 comprising a rounded tip 154. The radial distance of the second reverse barb 152 is greater than the radial size of the intima layer 56 of the artery 52. Thus, when the instrument 150 is manipulated essentially as described in respect to FIG. 24, the barb 152 stretches the intima outwardly away from the plaque 50, as shown at site 156, thereby at least somewhat disunifying the plaque 50 from the adventitia 60. The barb 132, which is disposed somewhat distal of the barb 152, is concurrently manipulated as describe in FIG. 24, thereby further disunifying the bond between the plaque and the artery, excavating the plaque and part of the arterial wall and ultimately removing the excavated plaque and excavated arterial wall from the artery.

Figure 25A:
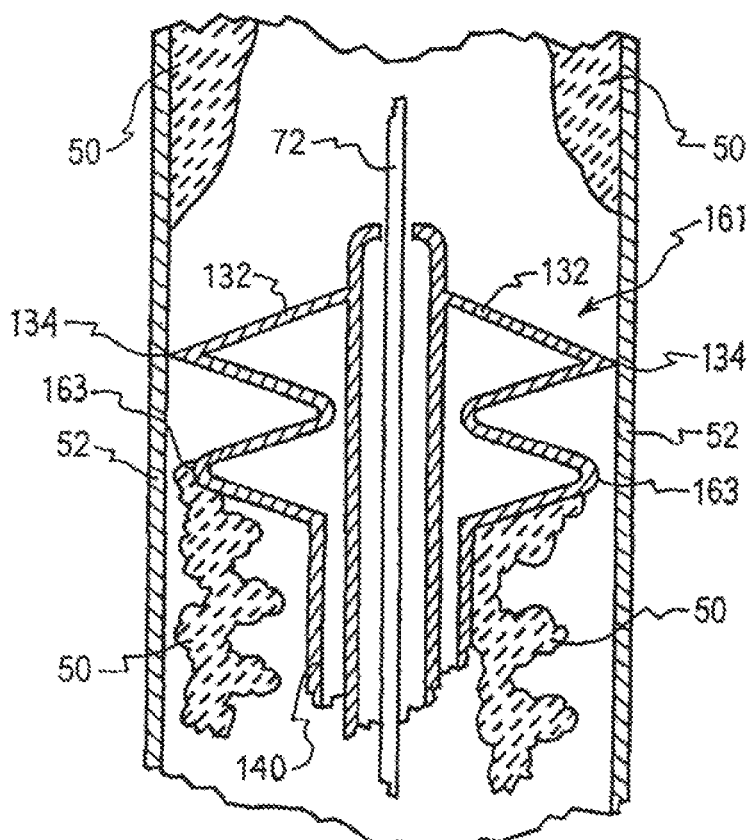
FIG. 25A is a longitudinal cross section of an artery wherein plaque is being removed by still another instrument.

Reference is now made to FIG. 25A, which shows an instrument, generally designated 161, having plaque engaging bellows of equal size on opposite sides of the tips 134 of the device 161. It is understood that these features may be two features oppositely situated, or four features evenly spaced around the circumference, or circumferential extendable features able to engage the plaque 50 on all sides simultaneously. The features are illustrated in the barbs 134, which have engaged the plaque and are removing the plaque 50. The plaque 50 barbs 134, which is being displaced down the vessel toward the arteriotomy and, due to resistance from both the friction with the Bessel wall and resistance from the plaque further ahead of the pushing force, the plaque 50 forms an accordionlike series of folds 163 as the device 161 is pulled back towards the arteriotomy. In this embodiment, plaque removal is facilitated by previous disunification of the plaque, which has led to the plaque being debonded from the vessel wall so that the excavation step illustrated in FIG. 25A does not also have to perform the debonding step.

Figure 26:
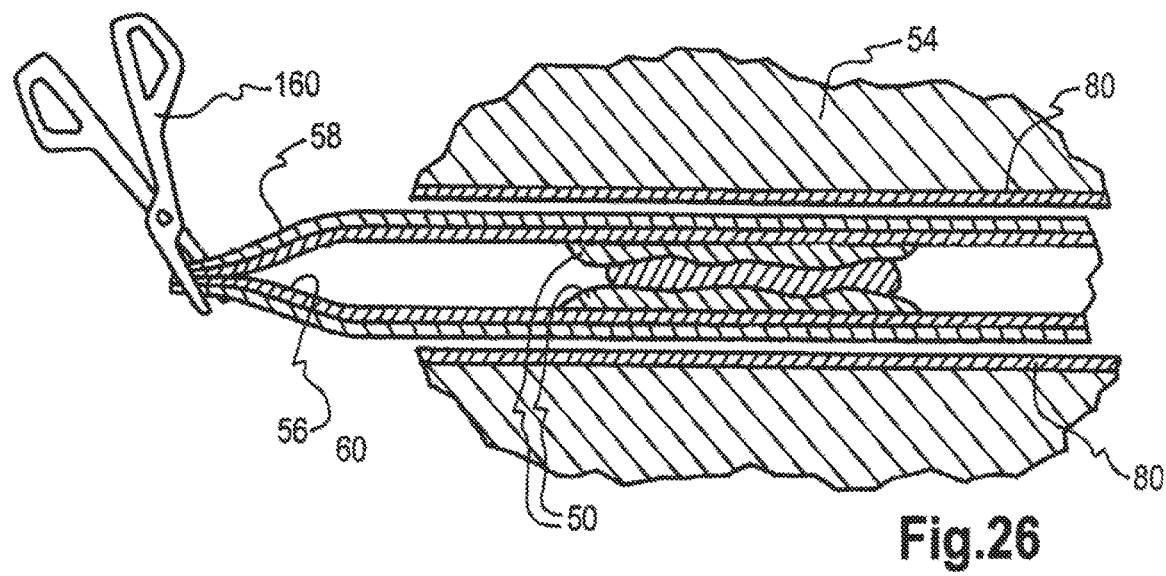
FIG. 26 illustrates, in longitudinal cross section, utilization of forceps for removing an annular section of plaque from an artery through an arteriotomy after excavation.

Reference is now made to FIG. 26, which illustrates one way of removing excavated plaque from an artery utilizing forceps 160. The elongated, long-nosed forceps 160, by closing the forceps along the excavated proximal ends of the intima and media, as shown in FIG. 26, the excavated portion within the artery is available to be grasped, pulled and removed through the arteriotomy. Of course, when using the instruments 130 and 150, it is not necessary to use forceps 160.

Figure 27:
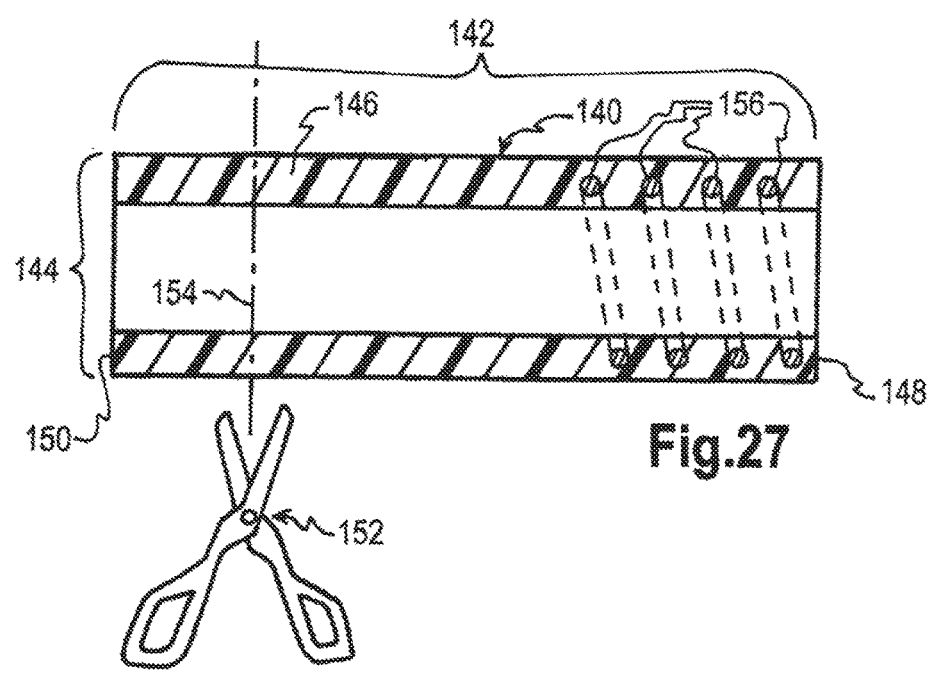
FIG. 27 illustrates, in longitudinal cross section, a tubular stent/graft of excessive length used to insure full coverage of an excavated artery so as to prevent or alleviate restenosis and to prevent occlusion by a plaque flap and including an encased distal end expandable stent comprising a helical coil.

Reference is now made to the FIGS. 27-34, which concern utilization of the tubular stent/graft to fully cover an excavated wall of an artery. The preferred material of choice comprises expanded polytetrafluoroethylene, of medical grade. To avoid utilization of two sections or segments of a tubular graft and the problems thereby created, it is preferred that a plurality of lengths and diametrical sizes be provided comprising tubular stent/grafts in inventory, such that any one of these tubular stent/grafts may be selected by the surgeon so as to be somewhat longer than the axial length of the excavated wall within the artery. One such tubular stent/graft, generally designated 140, is shown in FIG. 27. The tubular stent/graft 140 comprises an oversize length 142 and a suitable diameter 144, such that it may be radially expanded from a spaced position within the excavated artery to an expanded contiguous relationship with the interior surface of the excavated wall of the artery. The wall thickness of the tubular stent/graft 140 is selected, as would be apparent to those skilled in the art, to permit the permanent expansion, without damage to the tubular wall 146. While not mandatory, the tube 146 is shown as comprising blunt ends, namely a distal blunt end 148 and a proximal blunt end 150.

Once an overlength tubular stent/graft has been selected and the appropriate installation length identified by the surgeon, the proximal end 150 of the tube 146 is transversely severed by use of a suitable medical instrument, such as a pair of medical grade scissors 152 or a scalpel. This is illustrated as cut line 154. The cut line 154 may be either before installation into the artery or after the tubular stent/graft 140 has been partially inserted into the artery.

Figure 28:
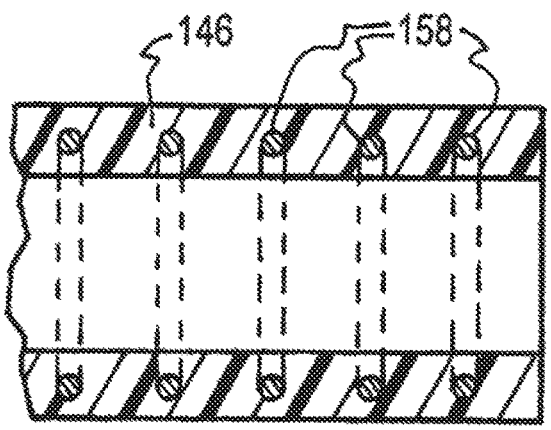
FIG. 28 is a fragmentary longitudinal cross-section of a distal end of a tubular stent/graft comprising encased reinforcement in the form of the spaced rings.

The distal end of the tube 146 comprises an encased expandable stent, which may be of any suitable medical type. In FIG. 27, an encased helical stent 156 is illustrated as exemplary, but other types of encased stents may be used, each able to accommodate not only radial expansion, but retention of the expanded position. The distal end of the tube 146 may, alternatively, comprise an encased or enclosed stent 158 comprising a series of parallel, radially directed rings 158. FIG. 28.

Figure 29:
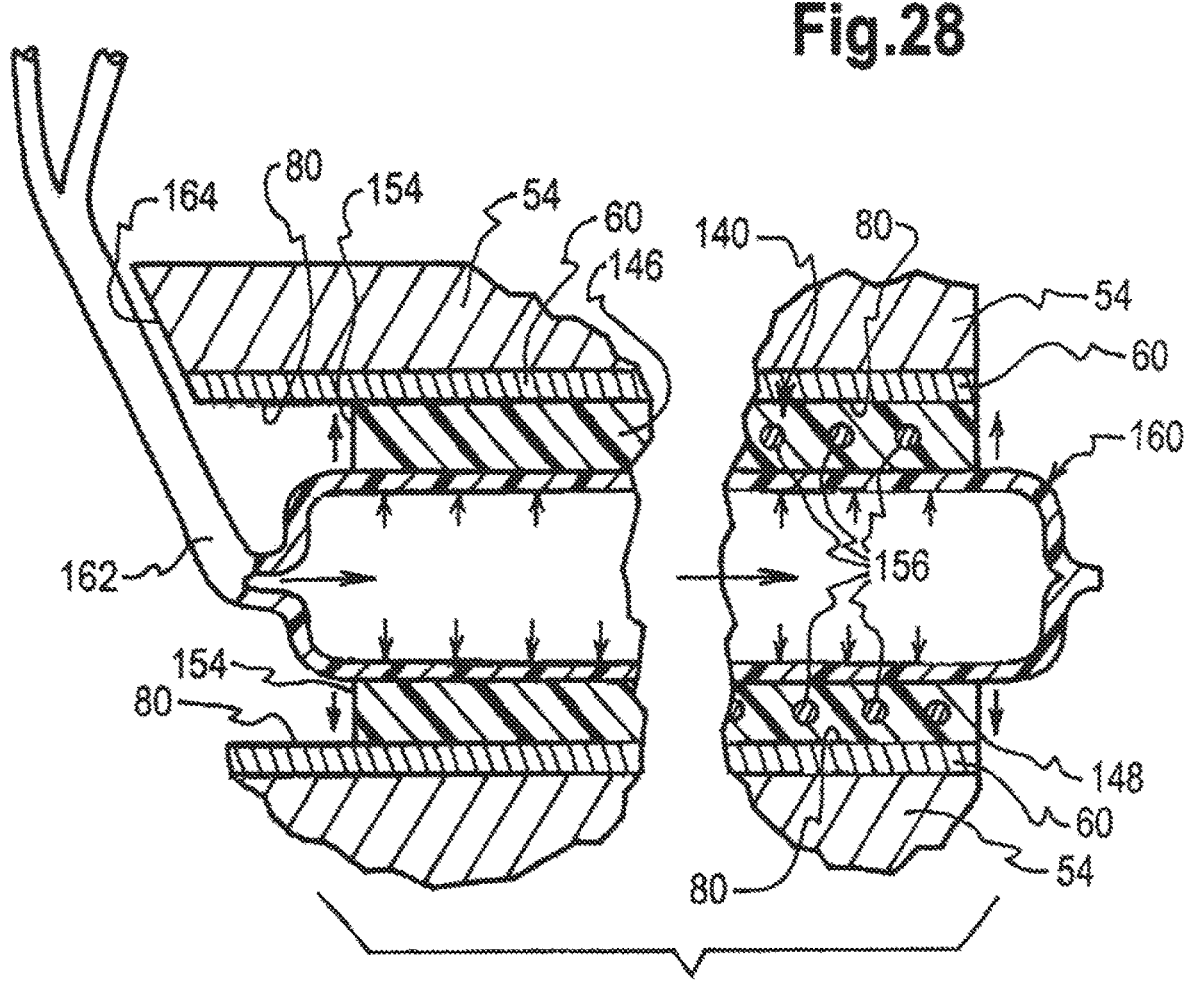
FIG. 29 is a fragmentary longitudinal cross-section of an excavated artery with an expanded tubular stent/graft positioned therein and mounted upon an inflatable balloon.

Typically, the initially-sized tubular stent/graft 140 is placed upon a deflated insertion balloon 160 in concentric relation and the two are inserted through the arteriotomy into and placed at the excavated part of the artery and inflated, as shown in FIG. 29. The insertion balloon, generally designated 160, after being inserted in a deflated condition, is inflated conventionally using an inflating/deflating tube 162, which extends through the arteriotomy 164, (through which the deflated balloon 160 and the non-expanded tubular stent/graft 140 were inserted) and advanced to the position shown in FIG. 29.

The expansion of tube 146 and stent 156 is a permanent expansion, such that the stent 156 encased in the distal end of the tube 146 takes a permanent set in the expanded position shown in FIG. 29, thereby holding the distal end of the tube 146 firmly and permanently against the adventitia 160 at interface 80. The stent may be either rigid or spring like, including spring like stents where the spring force holds the stent in the expanded position.

Figure 30:
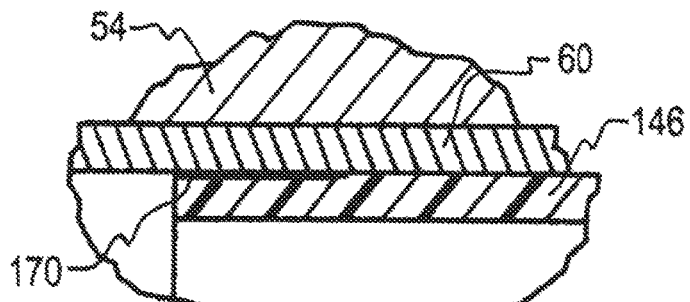
FIG. 30 is a fragmentary longitudinal cross-section showing retention using adhesive of the proximal end of expanded tubular graft placed in an excavated artery.
Figure 31:
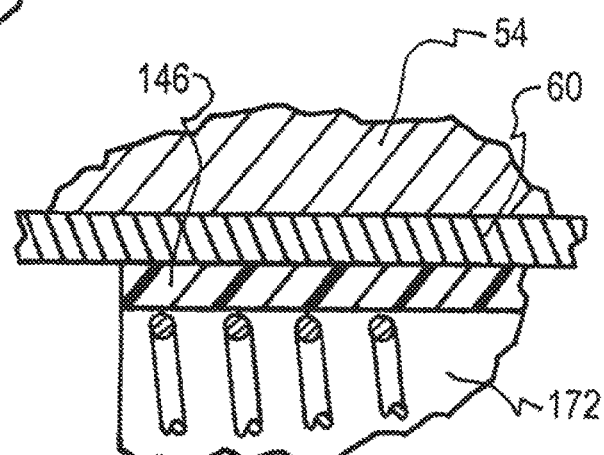
FIG. 31 is a fragmentary perspective showing a free or independent stent placed within the proximal end of an expanded tubular graft, by which the proximal end of the graft is held firmly and contiguously against the wall of an excavated artery.
Figure 32:
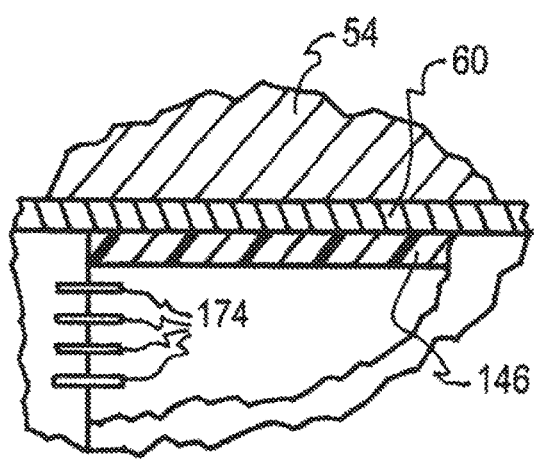
FIG. 32 illustrates in fragmentary longitudinal cross-section the use of staples at the proximal end of an expanded tubular graft placed in an excavated artery to firmly hold the proximal end of the graft contiguously against the excavated arterial wall.
Figure 33:
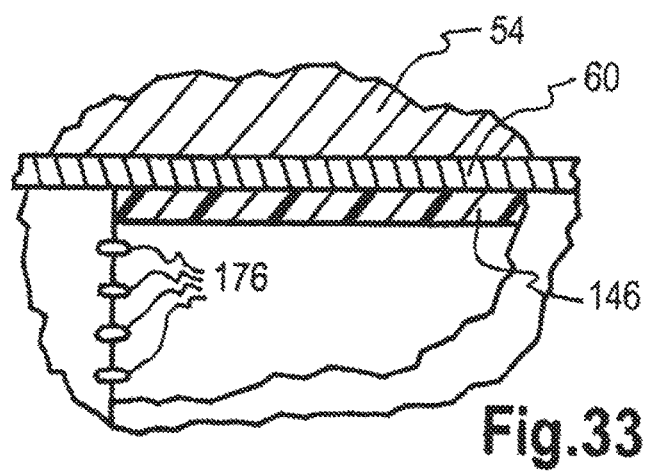
FIG. 33 illustrates in longitudinal cross-section retention, in an excavated artery, of the proximal end of an expanded tubular graft using sutures to hold the proximal end of the tubular graft firmly contiguous with the adjacent surface of an excavated artery.

The proximal end of the tube 146 is also firmly retained in its expanded condition contiguous with the interface 80. One way of doing this is illustrated in FIG. 30 wherein a suitable medical grade adhesive 170 is timely applied to the outside surface at the proximal end of the tube 146, typically before the tube 146 is expanded. It may also be applied to the directly adjacent surface of the excavated artery. A suitable independent stent 172 may be placed at the expanded proximal interior surface of the tube 146 after which the stent 172 is expanded permanently so as to continuously urge the tube 146 into its contiguous firmly retained relation with the adventitia 60. In the alternative, medical grade staples 174 may be placed so as to bridge the proximal portion of the tube 146 and the adventitia 60 to permanently position the proximal portion of the tube 146 in firm retained relation against the adventitia 60. FIG. 32. In the alternative, proximal sutures 176 may be used in lieu of staples, so as to be located in essentially the same bridging proximal positions. FIG. 33.

The invention may be embodied in other specific forms without departing from the spirit or essential characteristic thereof. The present embodiments, therefore, are to be considered in all respects as illustrative and are not restrictive, the scope of the invention being indicated by the appended claims rather than the foregoing description, and all changes which come within the meaning and range of equivalency of the claims are intended to be embraced.

What is claimed and desired to be secured by Letters Patent are:

1. A method of removing plaque from an artery, the method comprising:
   placing a loop of a ring stripper at an interface between an arterial wall and a plaque deposit within an artery, the interface having a diameter;
   while the loop is positioned at the interface, manipulating at least one wire of a pair of wires connected to the loop to expand a size of the loop at a distal end extending from a tubular sheath, the loop being extended from an initial size equal to the diameter of the interface to a larger size relative to the initial size, wherein manipulating the at least one wire comprises sliding the at least one wire relative to the tubular sheath; and
   dissecting plaque from the arterial wall by longitudinally displacing the loop to form an annular gap along the interface.

2. The method of claim 1, wherein manipulating the at least one wire to expand the size of the loop stretches the arterial wall away from the plaque deposit.

3. The method of claim 1, wherein the interface between the arterial wall and the plaque deposit is cylindrical.

4. The method of claim 1, wherein the loop comprises a pair of ends, each wire of the pair of wires being connected to a respective end of the pair of ends.

5. The method of claim 1, wherein manipulating the at least one wire comprises manually manipulating the at least one wire at a handle positioned at a proximal end of the tubular sheath.

6. The method of claim 1, further comprising manipulating the at least one wire of the pair of wires to reduce the size of the loop.

7. The method of claim 1, wherein manipulating the at least one wire comprises manipulating both wires of the pair of wires to expand the size of the loop that extends beyond the tubular sheath.

8. The method of claim 1, wherein the loop is concentric with the artery at the initial size and at the larger size.

9. A method of ring stripping, comprising:
   positioning a single loop having proximal ends integral with distal ends of a two shape-retaining wires of an elongated manual control;
   manipulating at least one of the proximal ends to cause the single loop to form an initial size consistent with a diameter of a cylindrical interface between an arterial wall and a plaque deposit within an artery;
   locating the single loop at the cylindrical interface;
   expanding the initial size of the single loop to an enlarged size by manipulating at least one wire of the two shape-retaining wires to stretch the arterial wall away from the plaque deposit; and
   displacing the single loop in a distal direction to debond the plaque deposit from the arterial wall.

10. The method of claim 9, wherein the single loop bluntly debonds plaque from the arterial wall via a force applied by the single loop in a radial direction.

11. The method of claim 9, wherein the at least one wire is manipulated through an elongated sheath.

12. The method of claim 9, wherein displacing the single loop stretches the arterial wall outwardly and urges the plaque deposit inwardly.

13. The method of claim 9, wherein stretching the arterial wall away from the plaque deposit includes forming an annular gap between an adventitial wall of the artery and a medial wall of the artery.

14. The method of claim 9, wherein the single loop is concentric with the artery in the initial size and in the enlarged size.

15. A method of ring stripping, comprising:
   positioning an adjustable loop at a distal end of a tubular sheath at a cylindrical interface between an arterial wall and a plaque deposit within an artery;
   positioning a pair of control wires through the tubular sheath with the pair of control wires respectively connected to a pair of loop ends of the adjustable loop;
   manipulating, when at the cylindrical interface, at least one control wire of the pair of control wires to adjust the adjustable loop between a first size and a second size, wherein manipulating the at least one control wire comprises manually manipulating the at least one control wire at a handle positioned at a proximal end of the tubular sheath; and
   dissecting artery tissue by advancing the adjustable loop along the cylindrical interface.

16. The method of claim 15, further comprising positioning a guide wire in the tubular sheath.

17. The method of claim 15, wherein manipulating the at least one control wire includes sliding the at least one control wire within the tubular sheath.

18. The method of claim 15, wherein dissecting the artery tissue comprises distally displacing the adjustable loop along the cylindrical interface.

\* \* \* \* \*